(12) United States Patent
Kim et al.

(10) Patent No.: US 12,114,910 B2
(45) Date of Patent: Oct. 15, 2024

(54) SUCTION ACTUATED ELECTROCAUTERY AND SUCTION DEVICE

(71) Applicant: Children's Medical Center Corporation, Boston, MA (US)

(72) Inventors: Heung Bae Kim, Weston, MA (US); Gabriel J. Ramos-Gonzalez, San Juan, PR (US); Alexander Yang, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 785 days.

(21) Appl. No.: 17/057,229

(22) PCT Filed: May 20, 2019

(86) PCT No.: PCT/US2019/033047
§ 371 (c)(1),
(2) Date: Nov. 20, 2020

(87) PCT Pub. No.: WO2019/226512
PCT Pub. Date: Nov. 28, 2019

(65) Prior Publication Data
US 2021/0204994 A1     Jul. 8, 2021

Related U.S. Application Data

(60) Provisional application No. 62/752,183, filed on Oct. 29, 2018, provisional application No. 62/675,472, filed on May 23, 2018.

(51) Int. Cl.
*A61B 18/08* (2006.01)
*A61B 18/00* (2006.01)

(52) U.S. Cl.
CPC .. *A61B 18/082* (2013.01); *A61B 2018/00172* (2013.01); *A61B 2018/00184* (2013.01);
(Continued)

(58) Field of Classification Search
None
See application file for complete search history.

(56) References Cited

U.S. PATENT DOCUMENTS 3,906,955 A    9/1975  Roberts
4,562,838 A    1/1986  Walker
(Continued)

FOREIGN PATENT DOCUMENTS

EP         1 902 682 A2    3/2008

OTHER PUBLICATIONS

International Search Report and Written Opinion for International Application No. PCT/US2019/033047, mailed Aug. 2, 2019.
(Continued)

*Primary Examiner* — Ronald Hupczey, Jr.
(74) *Attorney, Agent, or Firm* — Wolf, Greenfield & Sacks, P.C.

(57) ABSTRACT

An electrocautery device with a retractable suction tube is described. The electrocautery device includes a suction tube assembly that can move between an extended or retracted position using vacuum force generated by a suction source. In some embodiments, the suction tube assembly automatically locks into the extended position when extended such that axial force cannot cause the suction tube assembly to retract. The device may be suitable for use in laparoscopic procedures. The suction tube may be coaxially aligned with the electrocautery tip.

21 Claims, 27 Drawing Sheets

(52) U.S. Cl.
CPC ............... *A61B 2018/00595* (2013.01); *A61B 2218/007* (2013.01); *A61B 2218/008* (2013.01)

(56) References Cited

U.S. PATENT DOCUMENTS

| | | | |
|---|---|---|---|
| 4,719,914 | A | 1/1988 | Johnson |
| 4,919,129 | A | 4/1990 | Weber, Jr. et al. |
| 5,195,959 | A | 5/1993 | Smith |
| 5,318,565 | A | 6/1994 | Kuriloff et al. |
| 5,413,575 | A | 5/1995 | Haenggi |
| 5,449,357 | A | 9/1995 | Zinnanti |
| 5,951,581 | A | 9/1999 | Saadat et al. |
| 6,146,353 | A | 11/2000 | Platt, Jr. |
| 7,455,679 | B2 * | 11/2008 | Adams ............. A61B 17/32002 606/170 |
| 8,241,278 | B2 | 8/2012 | Sartor |
| 2003/0109802 | A1 * | 6/2003 | Laeseke ............. A61B 18/1477 600/564 |
| 2006/0264928 | A1 | 11/2006 | Kornerup et al. |
| 2011/0077645 | A1 | 3/2011 | Lin |
| 2013/0211438 | A1 * | 8/2013 | Dubois ............. A61B 17/1671 606/171 |
| 2013/0218186 | A1 | 8/2013 | Dubois et al. |
| 2015/0150580 | A1 | 6/2015 | Dubois et al. |
| 2015/0209100 | A1 | 7/2015 | Ineson |
| 2016/0262825 | A1 | 9/2016 | Jayaraj |
| 2018/0049729 | A1 | 2/2018 | Sullivan et al. |

OTHER PUBLICATIONS

International Preliminary Report on Patentability for International Application No. PCT/US2019/033047, mailed Dec. 3, 2020.

* cited by examiner

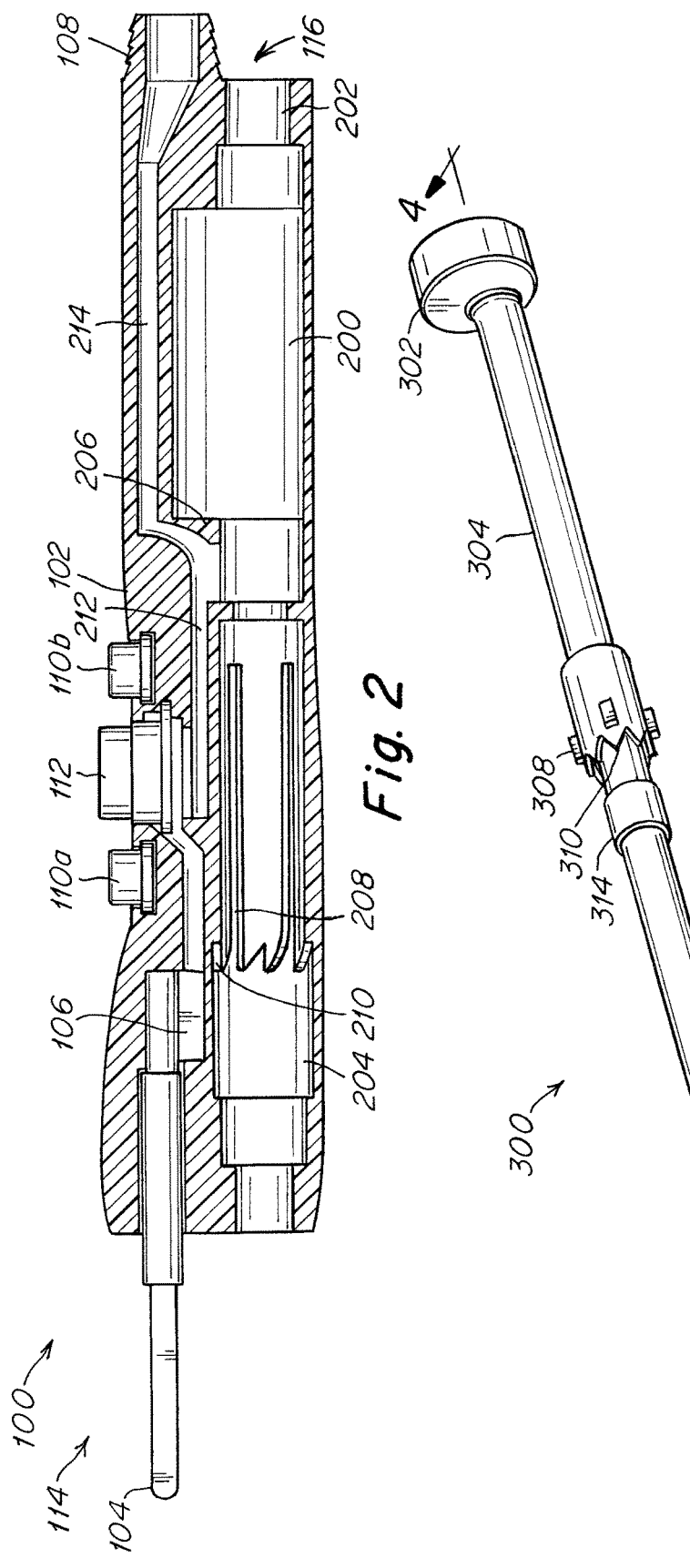
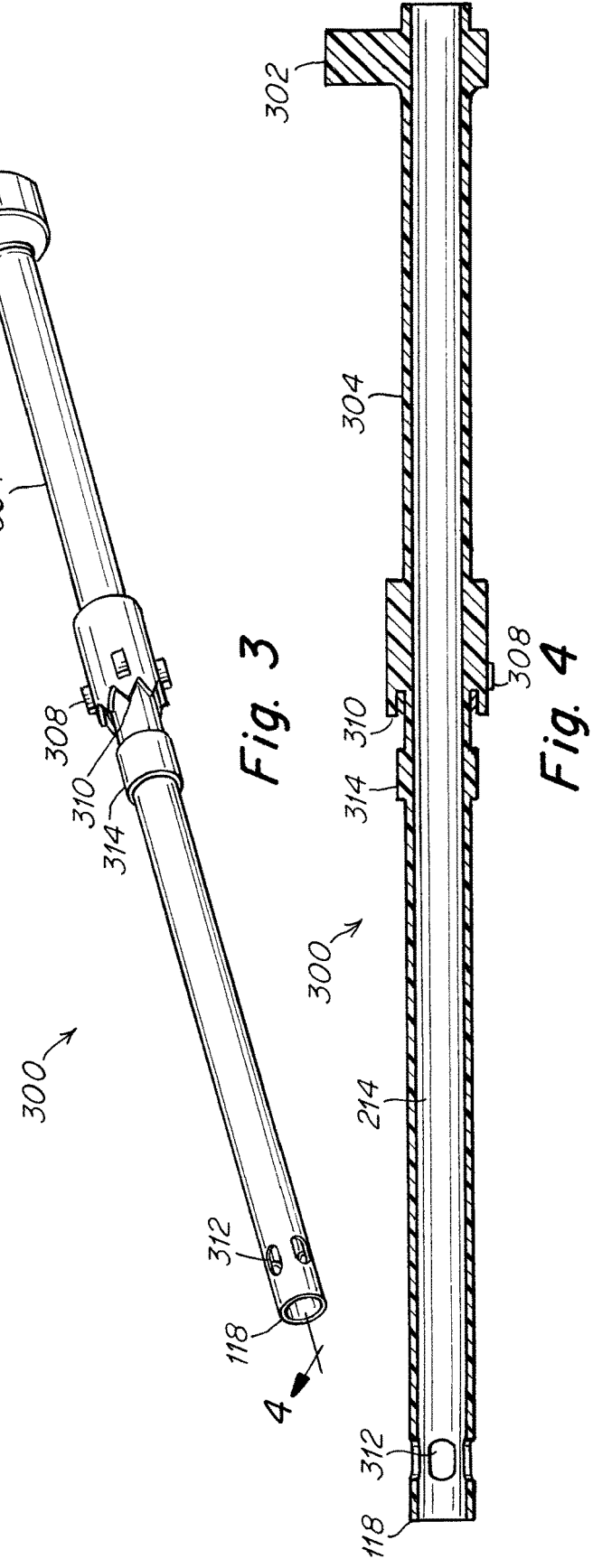
Fig. 2
Fig. 3
Fig. 4

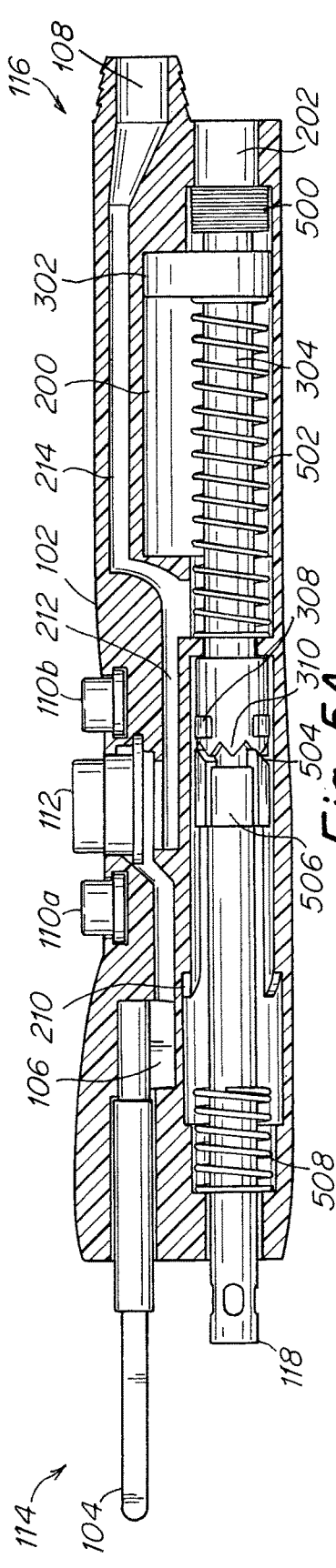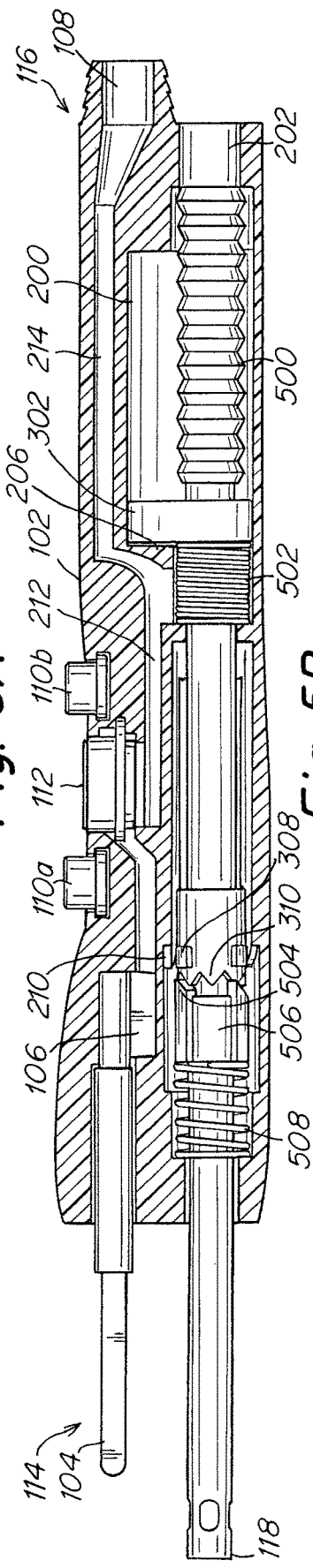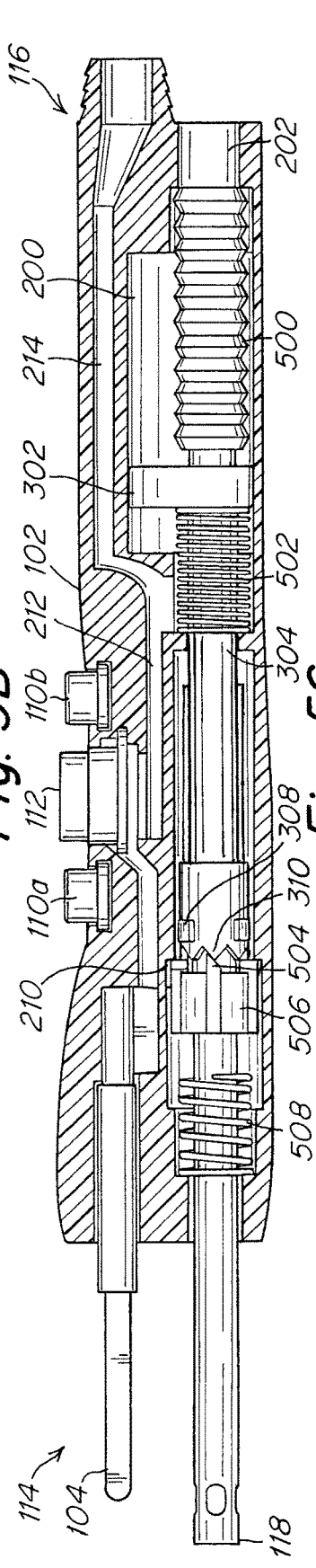

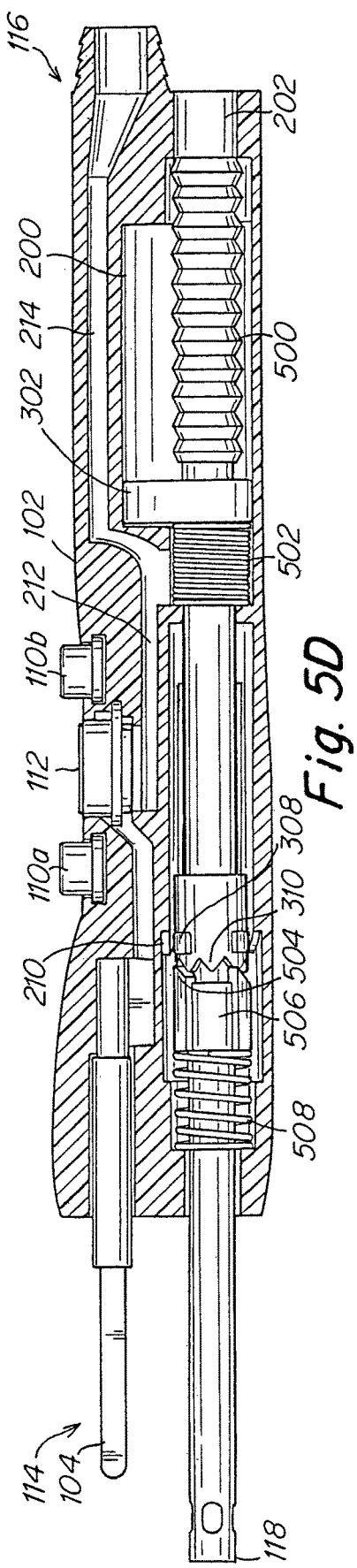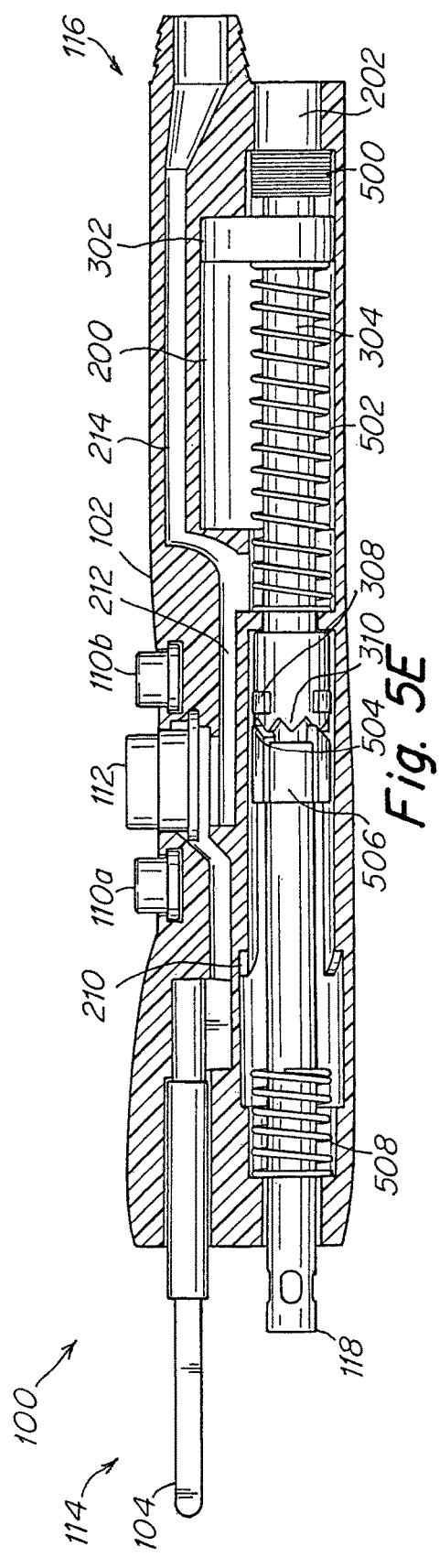

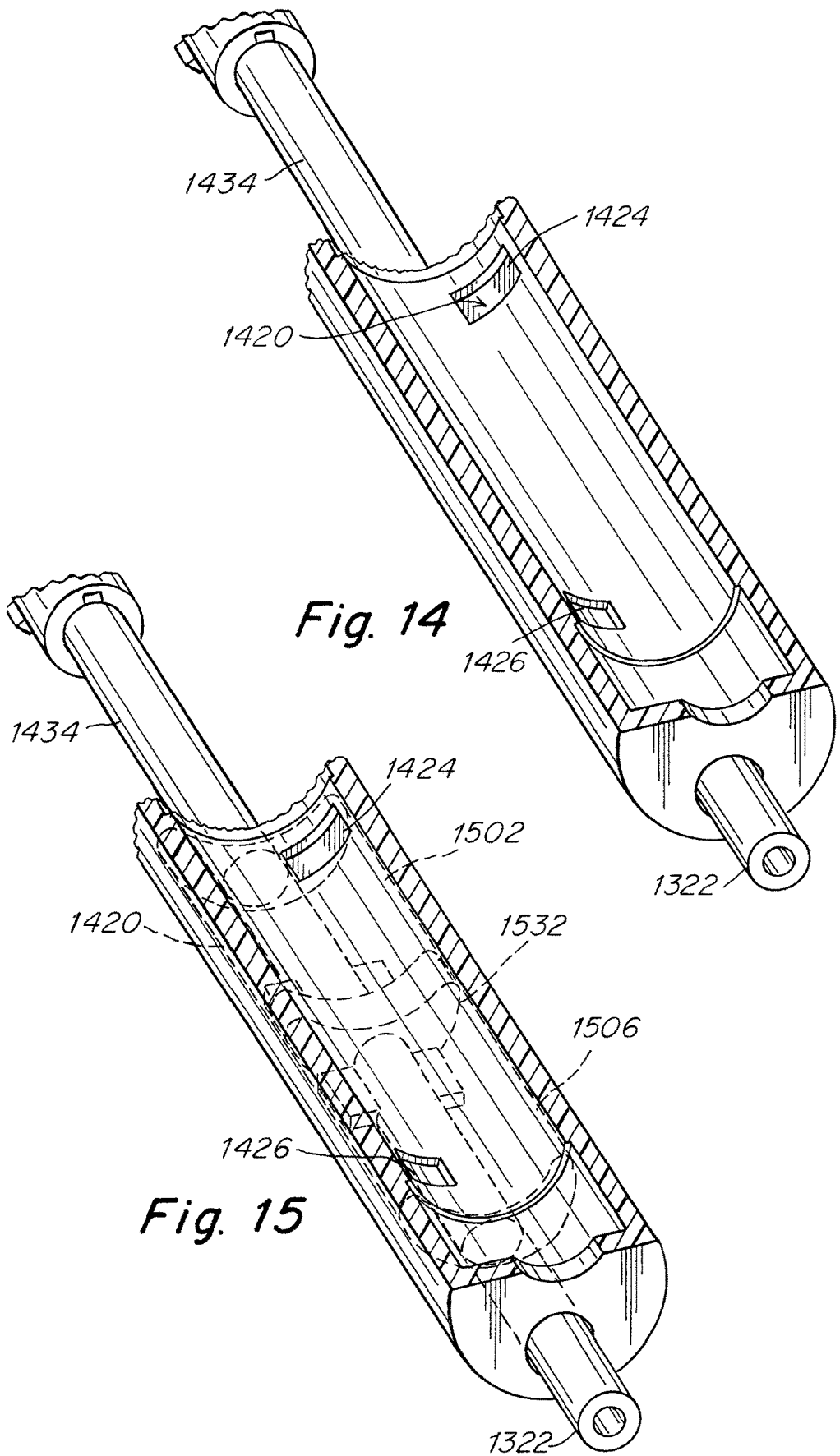

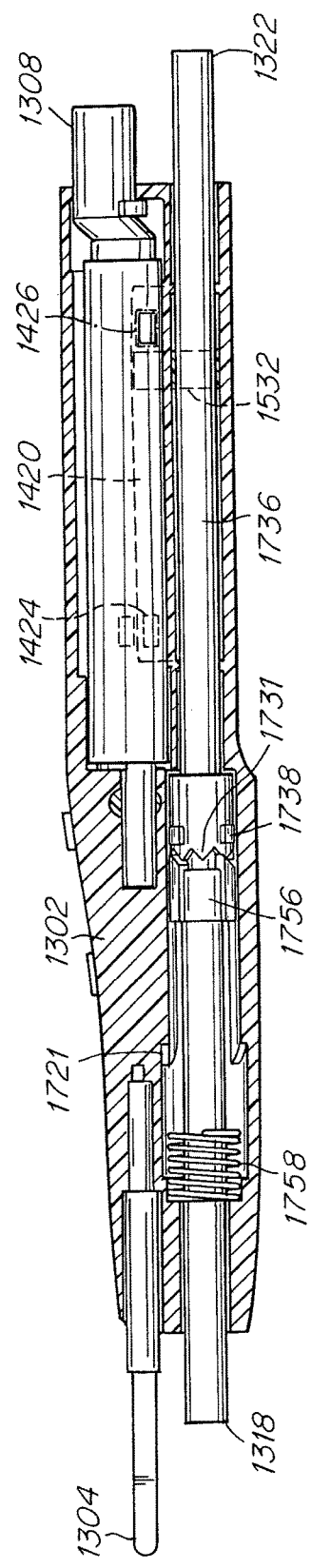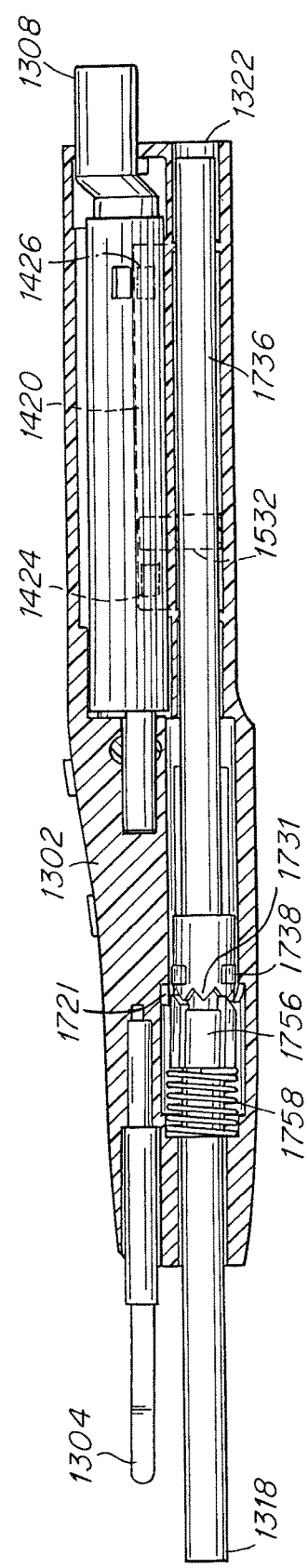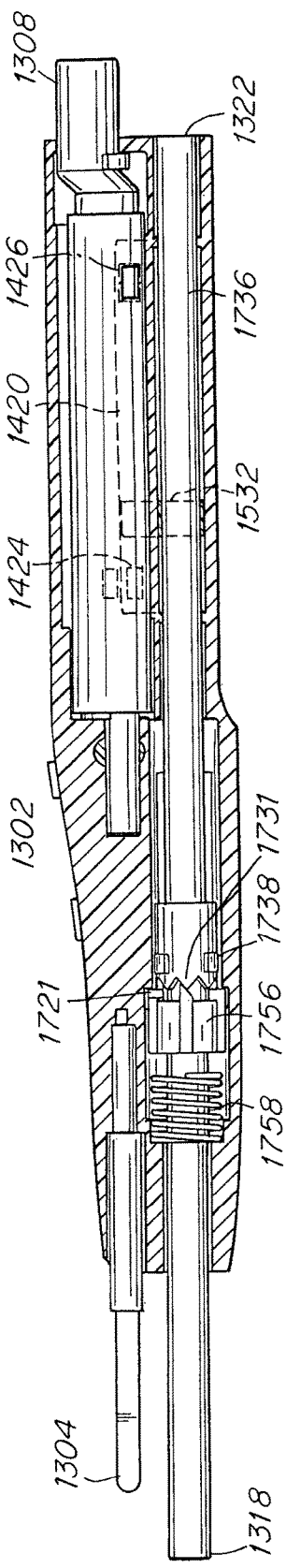
Fig. 17A
Fig. 17B
Fig. 17C

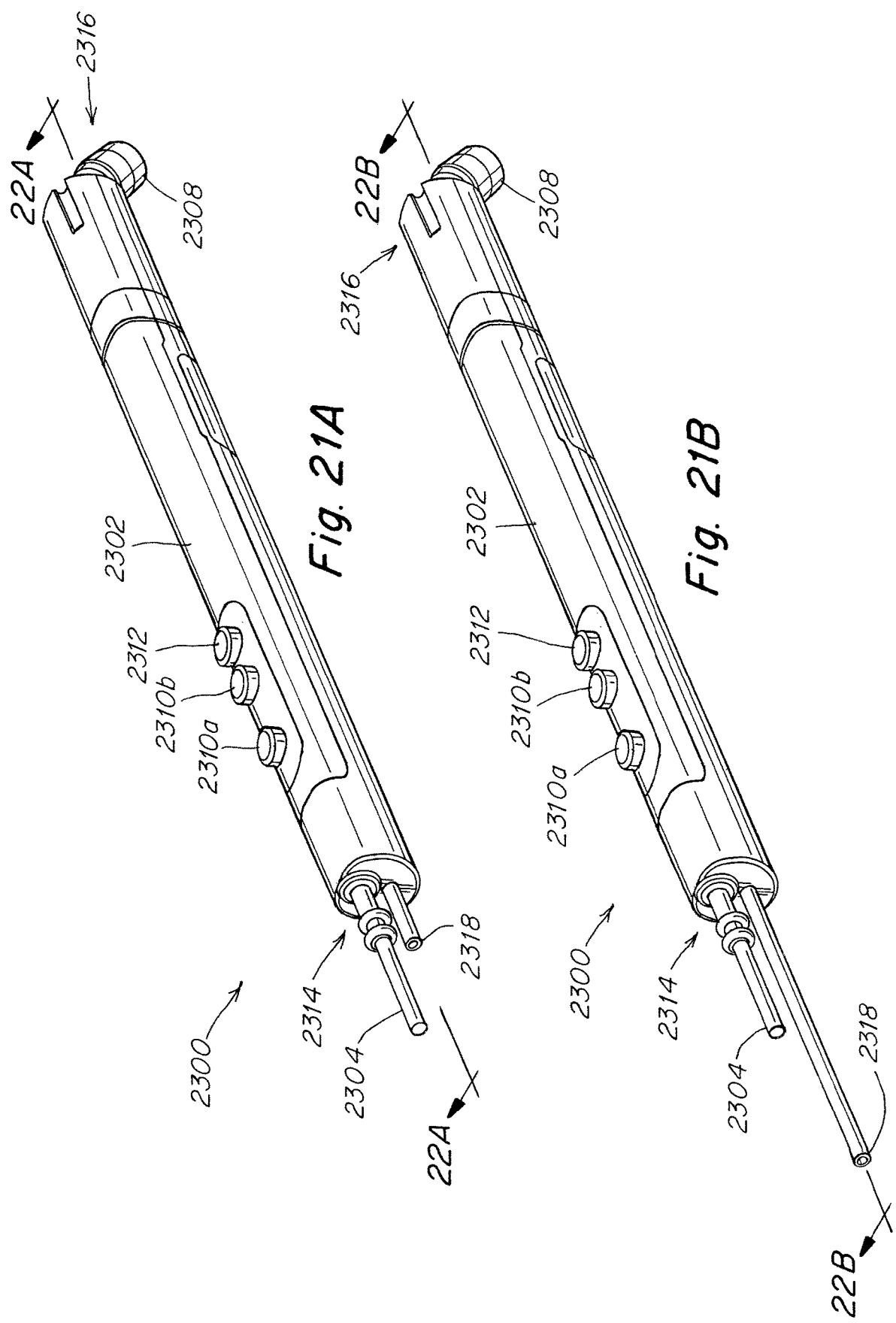

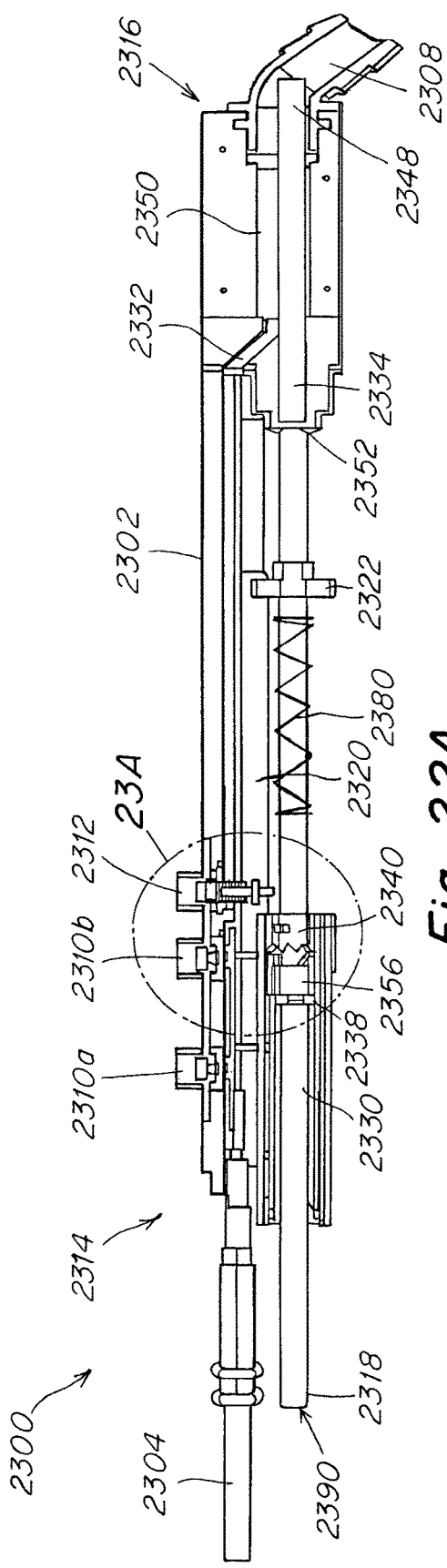
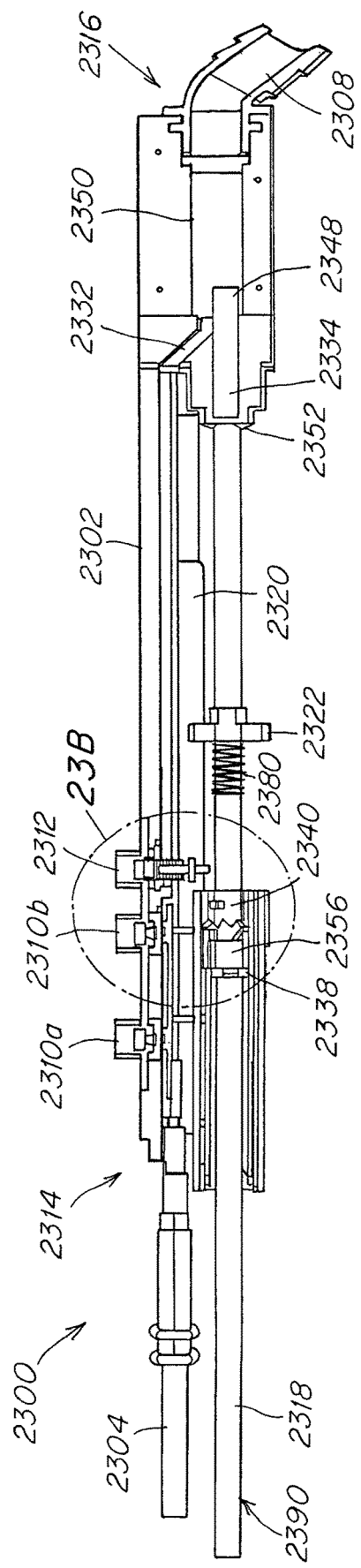

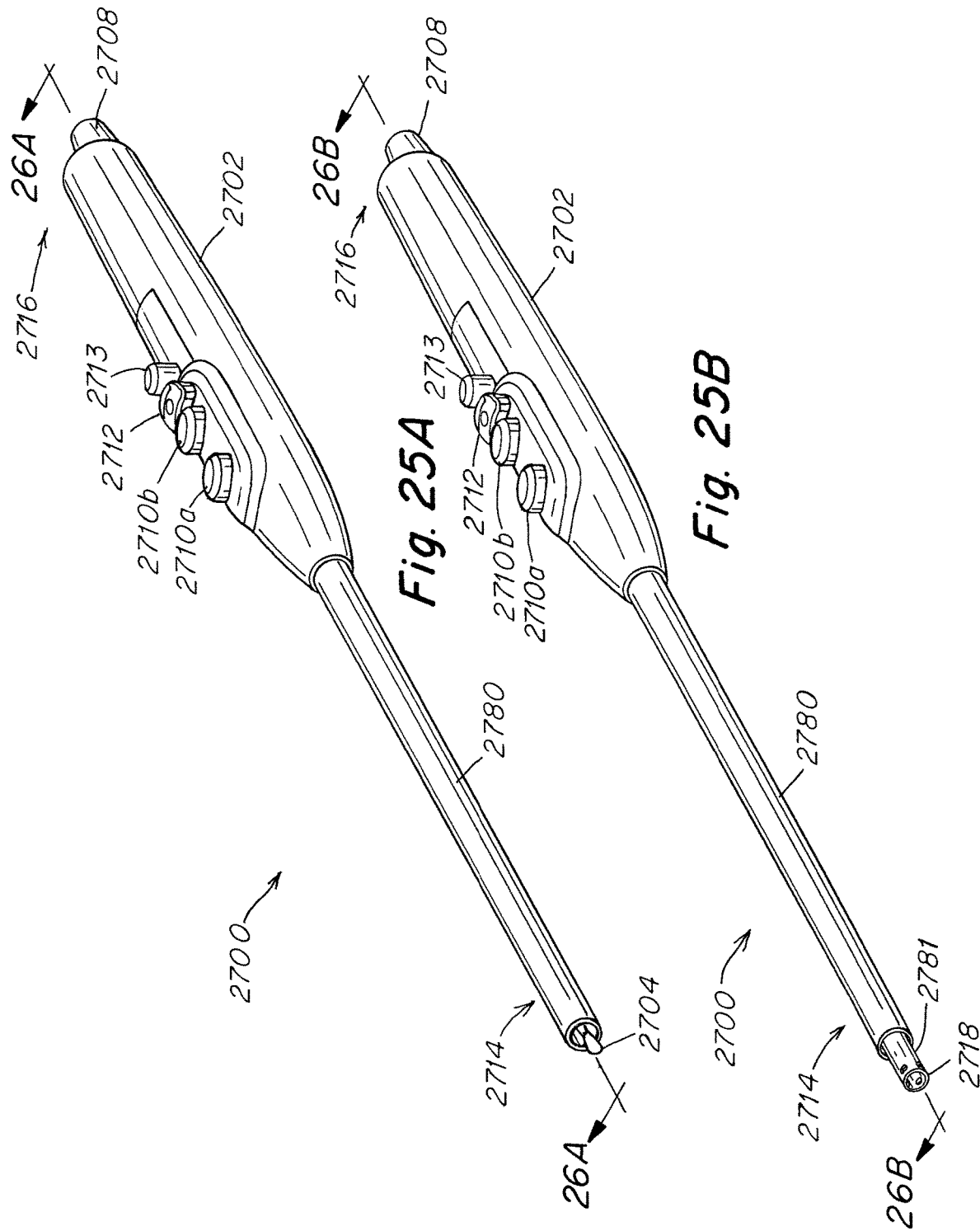

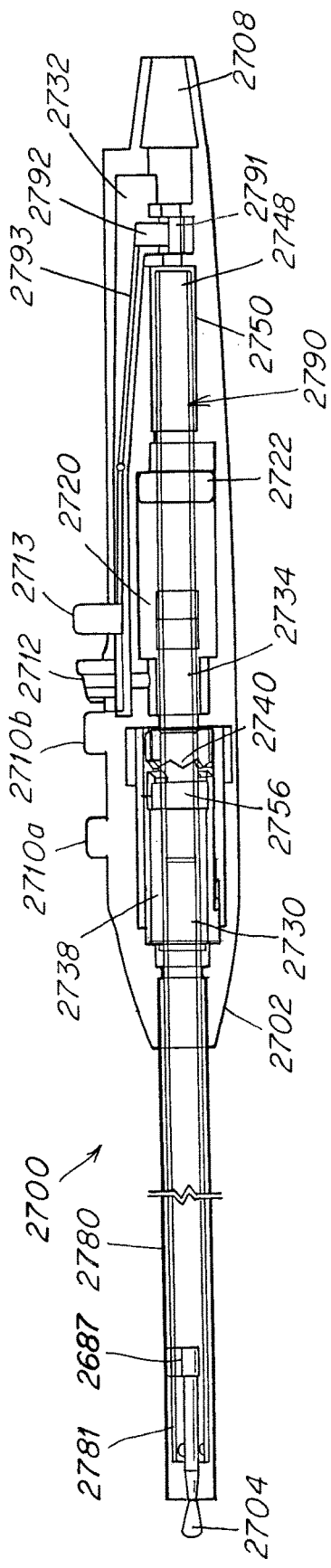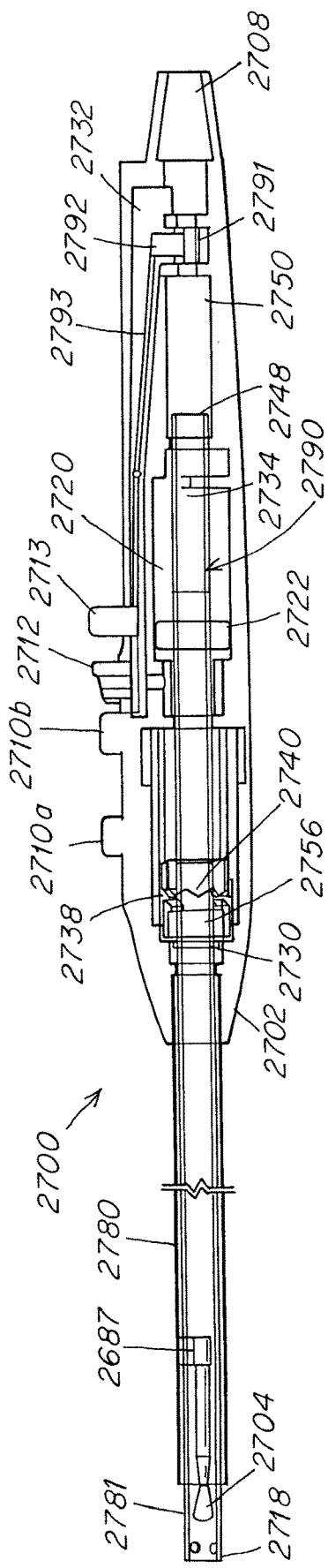
Fig. 26A
Fig. 26B

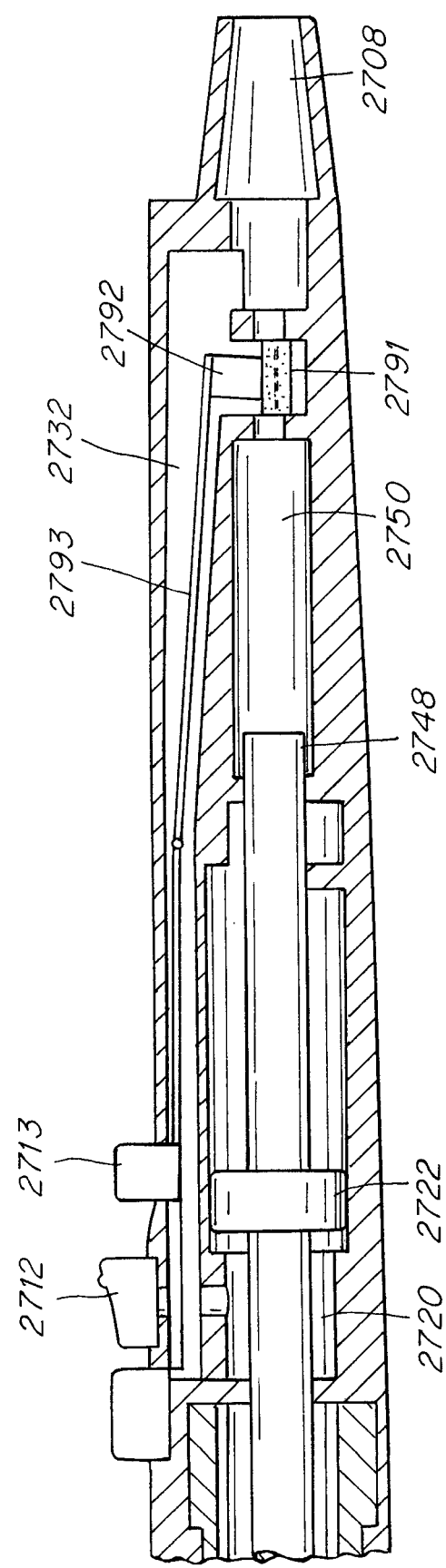
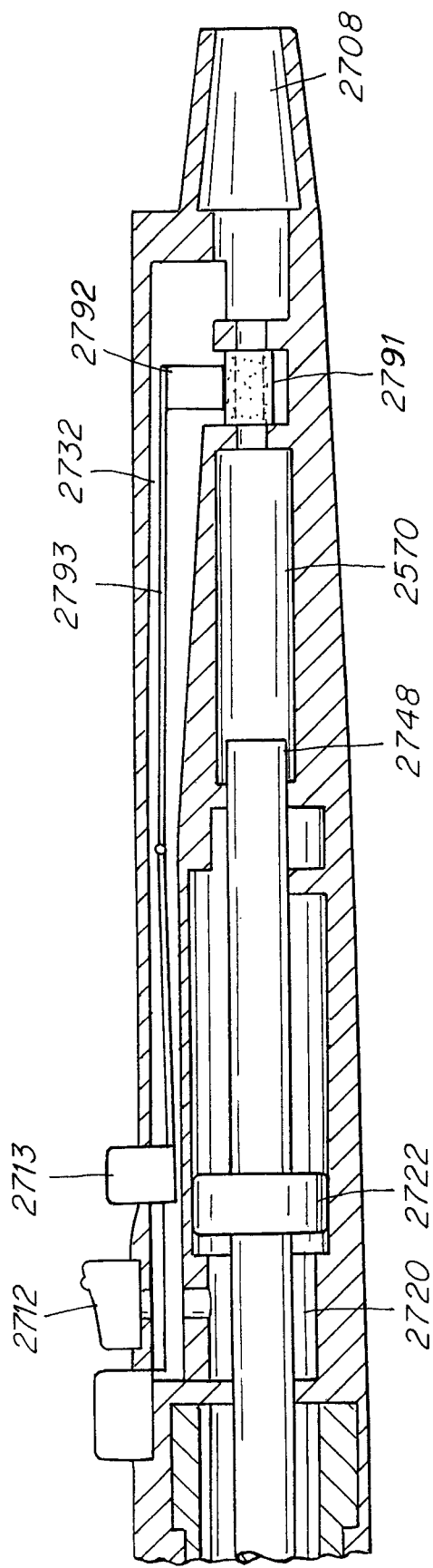
Fig. 27A
Fig. 27B

SUCTION ACTUATED ELECTROCAUTERY AND SUCTION DEVICE

RELATED APPLICATIONS

This application is a National Stage filing under 35 U.S.C. § 371 of International Application No. PCT/US2019/033047, filed May 20, 2019, which claims the benefit under 35 U.S.C. § 119(e) of U.S. Provisional Application No. 62/675,472, filed May 23, 2018, and U.S. Provisional Application No. 62/752,183, filed Oct. 29, 2018, the entire contents of each of which are incorporated by reference herein.

FIELD

Disclosed embodiments are related to electrocautery devices used during surgery.

BACKGROUND

Electrocautery wands are commonly employed during surgical procedures for manipulating and cutting tissue. During surgery, it is common for blood or other fluids to build up in the working environment as the local tissues are dissected, cut, or otherwise damaged. It is also common for smoke to be released when the electrocautery tip makes contact with tissue. Both fluid accumulation and smoke release obstruct the surgeon's field of vision, hindering progress and efficiency of the surgery. To rectify the issue, suction devices are often used by surgical assistants or personally by the surgeon to evacuate fluids and smoke from the surgical site.

SUMMARY

According to one embodiment of the electrocautery device, the electrocautery device includes the capability to suction. In this embodiment, the housing of the electrocautery device is connectable to a vacuum source and includes a suction cavity. An electrocautery tip is connected to the housing, as well as a suction tube with a suction tip. The suction tube is moveable from a retracted position to an extended position relative to the housing. The electrocautery device also includes an actuator constructed and arranged to selectively form a vacuum in the suction cavity. The vacuum source exerts a suction force on the suction tube assembly, causing the suction tip to move from the retracted position to the extended position.

In another embodiment of the electrocautery and suction device, the device includes a housing connectable to a vacuum source and a suction cavity. An electrocautery tip is connected to the housing. The device further includes a suction tube assembly including a suction tip moveable from a retracted position to an extended position relative to the housing. The suction tube assembly also includes a piston that defines a boundary between a front and rear suction region of the suction cavity. The device also includes an actuator constructed and arranged to selectively form a vacuum that can be diverted between the front suction region and rear suction region to cause the suction tip to move between the extended and retracted positions.

A method of operating an electrocautery and suction device includes providing an electrocautery and suction apparatus that comprises a housing that is connectable to a vacuum source and that contains a suction cavity in communication with a vent. The device also includes an electrocautery tip connected to the housing, a suction tube assembly moveable relative to the housing between an extended and retracted position, and an actuator constructed and arranged to selectively block communication between the vent and suction cavity. Triggering the actuator to reversibly block communication between the suction cavity and the vent to create a vacuum in the suction cavity such that the vacuum exerts a suction force on the suction tube assembly causes the suction tube assembly to shift from the retracted position to the extended position.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2 is a right side cross-sectional view of the electrocautery device taken along line 2-2 of FIG. 1B, with the suction tube assembly removed for clarity;

FIG. 3 is a top, right side, front perspective view of the suction tube assembly according to one embodiment;

FIG. 4 is a right side cross-sectional view of the suction tube assembly taken along line 4-4 of FIG. 3;

FIG. 5A is a right side cross-sectional view of the electrocautery device, with the suction tube assembly shown in the retracted position;

FIG. 5B is a right side cross-sectional view of the electrocautery device, with the suction tube assembly transitioning from the retracted position to the extended position;

FIG. 5C is a right side cross-sectional view of the electrocautery device, with the suction tube assembly locked in the extended position;

FIG. 5D is a right side cross-sectional view of the electrocautery device, with the suction tube assembly transitioning from the extended position to the retracted position;

FIG. 5E is a right side cross-sectional view of the electrocautery device, with the suction tube assembly returned to the retracted position;

FIG. 14 is a top, right side, rear cross-sectional view of the suction cavity and suction tube assembly of the electrocautery device taken along line 14-14 of FIG. 13;

FIG. 15 is a top, right side, rear cross-sectional view of the suction cavity and suction tube assembly of the electrocautery device of FIG. 13 with the suction tube shown in phantom;

FIG. 17A is a right side cross-sectional view of the electrocautery device taken along line 17A-17A of FIG. 13 in the retracted configuration;

FIG. 17B is a right side cross-sectional view of the electrocautery device of FIG. 13 in a hyperextended configuration while transitioning between the retracted and extended configurations;

FIG. 17C is a right side cross-sectional view of the electrocautery device of FIG. 13 locked in the extended configuration;

FIG. 21A is a top, right side, front perspective view of an electrocautery device according to one embodiment with a suction tube assembly in a retracted position;

FIG. 21B is a top, right side, front perspective view of the electrocautery device of FIG. 21A with the suction tube assembly in an extended position;

FIG. 22A is a right side cross-sectional view of the electrocautery device with the suction tube assembly in the retracted configuration, taken along line 22A-22A of FIG. 21A, with the lower housing removed for clarity;

FIG. 22B is a right side cross-sectional view of the electrocautery device with the suction tube assembly in the extended configuration, taken along line 22B-22B of FIG. 21B, with the lower housing removed for clarity;

FIG. 25A is a top, right side, front perspective view of the electrocautery device according to one embodiment with an inner tube in a retracted position;

FIG. 25B is a top, right side, front perspective view of the electrocautery device of FIG. 25A with the inner tube in an extended position;

FIG. 26A is a right side cross-sectional view of the electrocautery device of FIG. 25A taken along line 26A-26A;

FIG. 26B is a right side cross-sectional view of the electrocautery device of FIG. 25B taken along line 26B-26B;

FIG. 27A is an enlarged, right side cross-sectional view of the proximal end of the electrocautery device of FIG. 26A with suction turned off;

FIG. 27B is an enlarged, right side cross-sectional view of the proximal end of the electrocautery device of FIG. 26A with suction turned on;

DETAILED DESCRIPTION

Figure 1A:
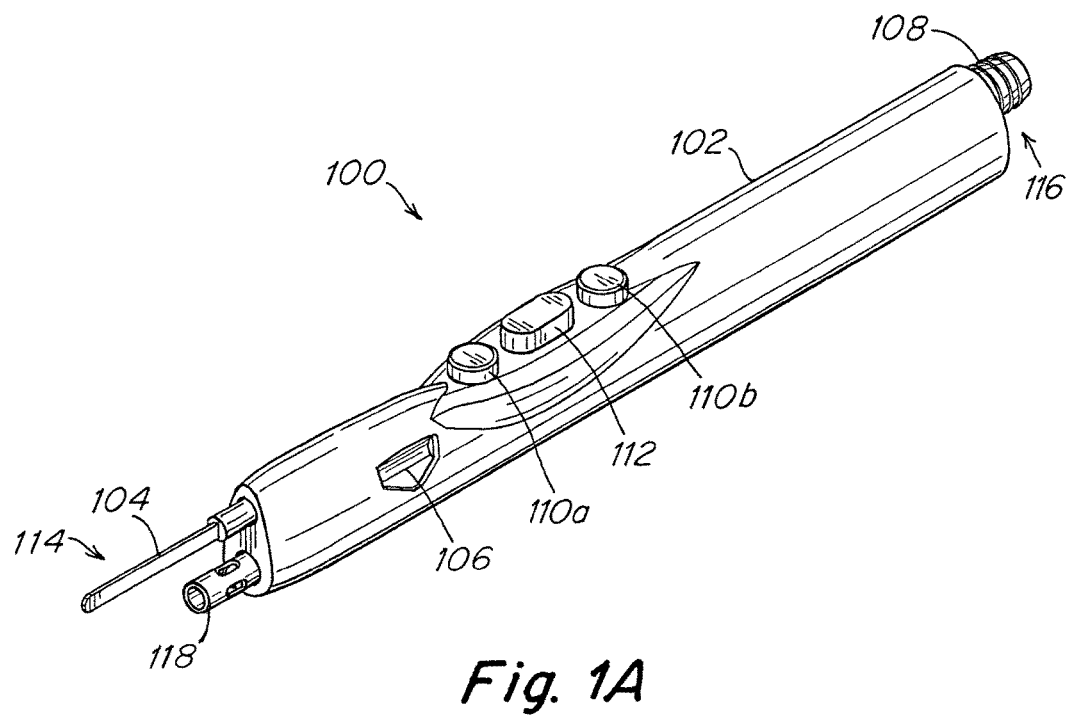
FIG. 1A is a top, right side, front perspective view of an electrocautery device according to one embodiment with a suction tube assembly in a retracted position.

Electrocautery wands, commonly known as "Bovies", with built in suction functionality have become known in the art. Such devices allow surgeons to cut, cauterize, and suction with the same device, alleviating the need to reach for a separate suction device or wait for a surgical assistant to clear the surgical site. Surgeons commonly use the suction tip of these combined electrocautery and suction devices to move tissue out of their way during procedures.

Many wands in the art have immobile suction tips that sit near the electrocautery tip. These designs can often block line of vision with the target site due to the effectively enlarged working tip. Additionally, many of these devices are designed solely for smoke evacuation. Other wands currently in the art have slidable suction tips that may be co-axial with the electrocautery tip or parallel to the electrocautery tip. These designs are commonly controllable via manual linear sliders on body of the wand. Because surgeons switch between suction and electrocautery tip use with significant frequency over the course of potentially very long procedures, the inventors have found that such designs tend to significantly fatigue the surgeons' fingers due to repetitive performance of the extended sliding motion required to extend and retract the tube. Electrocautery wands with electrically actuable suction tips have been considered, but the inventors have found that with current technology, adding the necessary motors to the wands would result in a wand that is too heavy and too bulky for prolonged use of a device that often requires prolonged concentrated precision. The inventors have contemplated that electrocautery wands with suction capability could be improved.

According to one embodiment, the electrocautery device is a generally elongate device that is easily graspable by a user. An electrocautery tip, capable of industry standard cutting and cauterizing functions, extends from a distal end of the electrocautery device. A suction tip is extendable from a distal end of the electrocautery device. The proximal end of the device can be connected to one or more suction sources depending on the embodiment. As will be described, the suction source is used both to generate a vacuum to remove smoke and fluids from the surgical environment, and to actuate the suction tube within the electrocautery device.

The electrocautery device has at least two operating configurations, a retracted configuration in which the suction tip is retracted relative to the electrocautery tip such that the electrocautery tip extends beyond the suction tip, and an extended configuration in which the suction tip extends beyond the electrocautery tip. In the retracted configuration, the user can cut and cauterize with the electrocautery device in a manner well known in the art. When the user desires to focus on suctioning, the user can actuate a button on the electrocautery device, which triggers the blocking or diversion of airflow within the device depending on the embodiment. The change in airflow creates or diverts a vacuum within the electrocautery device to move the suction tube from the retracted position to the extended position, or from the extended position to the retracted position. With the suction tip in the extended position, the user can easily suction the working environment without interference from the electrocautery tip. When the user wants to revert to cutting or cauterizing, the user simply actuates the button again, causing the suction tube assembly and suction tip to retract to the retracted position, returning the entire device to the retracted configuration.

A vacuum actuated suction tube actuating mechanism obviates the need to burden the electrocautery device with motors, and also allows the user to switch configurations by simply toggling a button or switch, alleviating fatigue issues that can commonly occur with the hand-actuated systems currently known in the art.

According to one embodiment, the electrocautery device includes a housing containing a suction cavity connectable to a suction source, a vent in the housing that is connected to the suction cavity, an electrocautery tip that extends from the housing, and a suction tube assembly that extends from the housing and is connectable to a suction source. Buttons or other user interface elements on the housing control the delivery of current to the electrocautery tip. Another button or other toggling mechanism can be triggered by a user to selectively block access between the vent and the suction cavity. When vent access is blocked, the suction cavity is connected only to the suction source, producing a vacuum in the suction cavity by effectively evacuating air from the suction cavity. The presence of the vacuum acts on the suction tube assembly, causing it to shift from a retracted position to an extended position, or from the extended position to the retracted position as detailed below.

Some surgeons prefer to use the suction tip of an electrocautery wand to dissect tissue during surgery. When used in such a manner, the suction tip is routinely exposed to forces that would normally cause the suction tip to retract. The inventors have contemplated that having a suction tip that can be physically locked in an extended position would allow surgeons to continue the practice of dissecting with the suction tip without having to be concerned about the suction tip from inadvertently moving.

In some embodiments of the suction tube assembly, the assembly includes a "click-lock" mechanism that allows the suction tube assembly to be locked in the extended position. The click-lock mechanism is similar to the mechanism found in a retractable ballpoint pen. In these embodiments, the suction tube assembly comprises a cam, and contiguous suction tube with a suction tip end ("suction tip"), and a piston end outfitted with a piston.

When the suction tube assembly is in the retracted position, the piston is spring biased by a proximal spring towards the proximal end of the suction cavity. When the vacuum is formed in the suction cavity, a vacuum force acts on the piston, overcoming the spring force, causing the piston to slide to the distal end of the suction cavity, compressing the proximal spring. As the piston slides towards the distal end of the electrocautery device, it contacts the cam and pushes the cam distally against a distal spring that biases the cam in the proximal direction. The spring force prevents the cam from sliding distally further, but the continued pushing from the piston causes the cam to rotate about the longitudinal axis of the suction tube assembly into alignment with locking grooves of the device housing.

When the user releases the button, air access between the vent and the suction cavity is restored, allowing environmental air to access the suction chamber. This alleviates the vacuum in the chamber, eliminating the vacuum force and allowing the proximal spring to return the piston to its original position at the proximal end of the suction cavity. Without the piston pressing against the cam, the cam slides with the suction tip in the proximal direction, becoming partially trapped in the locking grooves within the housing. The trapping of the cam in the locking grooves prevents the suction tube assembly from being returned to the retracted position, thereby securing the suction tip in the extended position. As such, during the process of moving from the retracted position to the extended position, the suction tip enters a hyperextended position before the user releases the suction, allowing the suction tube to come to rest in the locked extended position.

To unlock and retract the suction tip, the user simply actuates the same button again, blocking communication between the vent and the suction cavity. The re-formation of the vacuum in the suction cavity again causes the piston to overcome the proximal spring force and slide distally. The locking grooves prevent the cam from sliding proximally, but not distally. Consequently, as the suction tube slides distally, it pushes the cam distally, causing the suction tip to return to the hyperextended position and the cam contact the distal spring and rotate out of alignment with the locking grooves.

When the user releases the button, the vacuum is again alleviated, allowing the piston to be returned to the retracted position by the proximal spring. Since the cam was rotated out of alignment with the locking grooves, as the suction tube returns to its retracted position, the cam clears the locking grooves, thereby not obstructing the suction tube and allowing the tube to return to the retracted position. This returns the entire electrocautery device to its original retracted configuration.

In some embodiments of the electrocautery device, instead of relying on a proximal spring distally biasing a piston of the suction tube assembly back to the retracted position, alternative mechanisms are considered and the current application is not so limited. For instance, instead of a spring distal to the piston that biases the piston proximally, the device could instead utilize a spring attached to the proximal end of the device and the proximal end of the piston. In these embodiments, as the vacuum pulls the piston distally, the spring is extended as the piston slides forward. When the vacuum is alleviated, the extended spring pulls the piston back to the retracted position.

In other embodiments of the electrocautery device, as opposed to relying on the proximal spring to retract the piston, both the extension and the retraction of the suction tube assembly rely on vacuum force. In these embodiments, the suction cavity is divided into proximal and distal suction regions by the piston. Instead of obstructing airflow between a vent and the suction cavity, when the user triggers the toggle on the housing, the vacuum connection with the suction source is switched between the proximal suction region and the distal suction region. As a result, a vacuum is formed only on one side of the piston, forcing the piston to slide in the direction of the vacuum. As the piston slides, the size of the proximal and distal suction regions change depending on which way the piston is sliding. For example, if the vacuum was created in the distal suction region, then the piston slides in the distal direction, extending the suction tube assembly, enlarging the proximal suction region, and shrinking the distal suction region until the piston reaches the distal edge of the suction cavity.

Some embodiments of the electrocautery device rely on both the aforementioned split suction cavity and click-lock systems. In these embodiments, pressing a button on the housing creates a vacuum in the distal suction region causes the suction tube assembly to slide distally, causing the suction tube assembly to reach a hyperextended position and rotate a cam into or out of alignment with locking grooves on the housing. Releasing the button diverts the vacuum to the proximal suction region, causing the piston and suction tube assembly to slide in a proximal direction towards the vacuum. Depending on the rotational state of the cam, the proximal sliding of the suction assembly either slides the cam into the locking grooves, locking the suction tube assembly in an extended position, or slides the cam past the locking grooves, returning the suction tube assembly to the retracted position.

In one embodiment of the electrocautery device, a spring-loaded button on the housing of the electrocautery device controls a linear diverter connected to a suction source. When the user presses the button, the diverter shifts the suction between a proximal suction channel leading to the proximal suction region and a distal suction channel to the distal suction region. By pressing the button, the user diverts the vacuum between suction regions, allowing the user to retract or extend the tube.

Another embodiment of the electrocautery device includes a semi-lunar suction cavity with a proximal hole and distal hole in the top of the suction cavity. The proximal hole and distal hole are spaced such that they are on longitudinally and laterally opposite sides of the suction cavity. In this embodiment, when the user presses the spring-loaded button, a suction channel with corresponding proximal and distal holes "swings" laterally with respect to the suction cavity, about an axis, parallel to the longitudinal axis and intersecting the imaginary circular center (from which a radius would extend), of the semilunar suction cavity. In an "extend" configuration, the distal holes of the suction cavity and suction channel align, causing suction to be diverted to the distal suction region. In a "retract" configuration, the suction channel has swung to the laterally opposite side, aligning the proximal holes of the suction channel and suction cavity, diverting suction to the proximal suction region.

Another embodiment of the electrocautery device includes a rotary diverter shaped like an extruded circular sector that functions as a two way valve between a suction source and a proximal or distal channel leading to proximal and distal suction regions respectively. The rotary diverter has two configurations and rotates between them when a user presses the spring-loaded button. In the "retract" configuration, the diverter connects the proximal channel to the suction channel, allowing the suction source to create a vacuum in the proximal suction region. In the "extend" configuration, the diverter connects the distal channel to the suction channel, allowing the suction source to create a vacuum in the distal suction region.

In other embodiments of the suction tube assembly, the suction tube simply comprises an extended tube with a piston between the mid-point and the proximal end of the tube. A suction source is connected to the proximal end of the suction tube, while the distal end of the suction tube serves as the suction tip. In these embodiments, when a vacuum is created on the distal side of the piston, the vacuum acts on the piston and causes the suction tube to slide in the distal direction, extending the suction tip beyond the electrocautery tip. In some embodiments, the suction tube is retracted by diverting the vacuum to the proximal side of the piston. In other embodiments, the suction source is simply cut off or allowed to equilibrate with atmosphere, allowing a spring to return the suction tube to its original position.

It should be understood that although the previous mechanisms were described in relation to specifically shaped structures, the inventors have contemplated that other structures could be used to achieve the methods described above. The current application is not limited to the structures described. As a non-limiting example, the diverters described could be of any shape necessary to divert suction flow between suction regions. Similarly, the described channels could be multiple channels or a single internally divided channel. The described suction tube assembly could take on any form as long as it is capable of being retracted and extended. While suction from a suction source is described as the only form of actuation for the suction tube, other systems for back-up such as a linear slider or a wheel and ratchet system are also contemplated. Similarly, any appropriate locking system could be used in place of the click-lock system. The inventors contemplate that spring-biased locking pins, friction fittings, non-spring biased pins, and retractable obstructing members on one or both of the housing or tube could be employed as the current disclosure is not limited in this respect.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
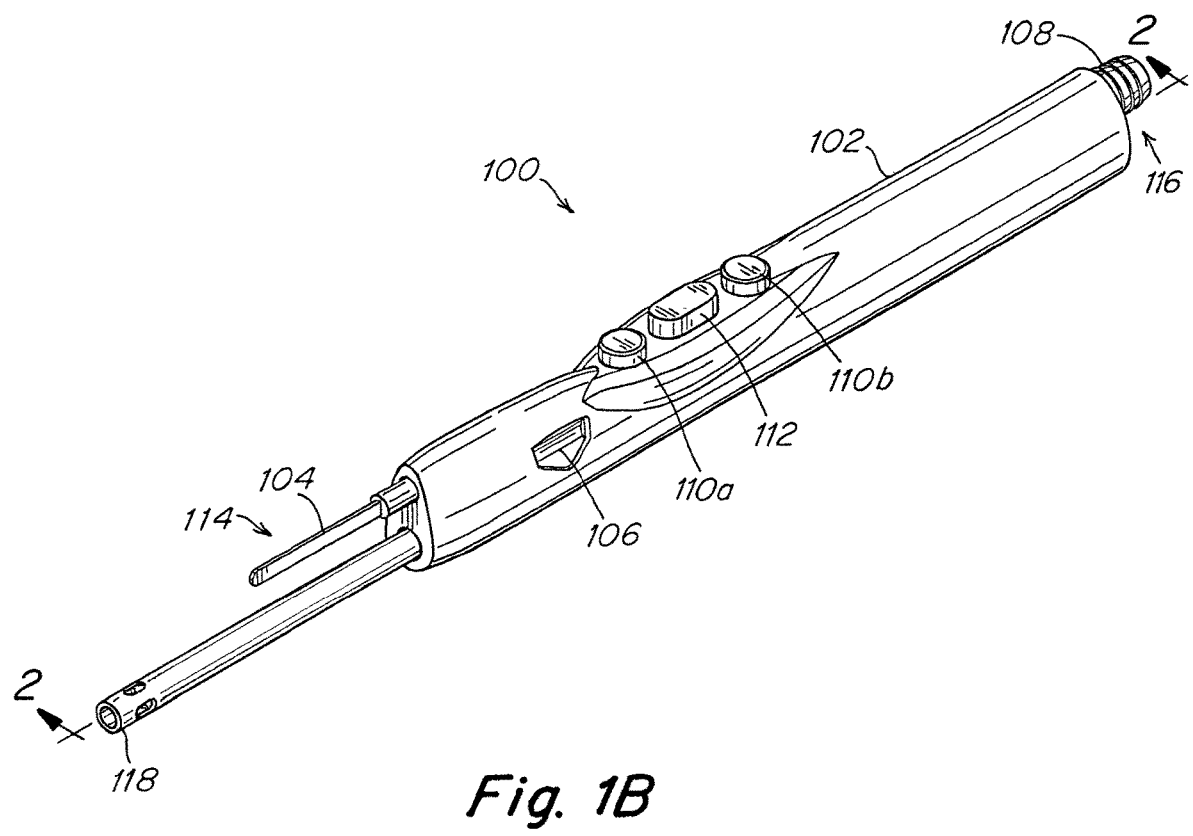
FIG. 1B is a top, right side, front perspective view of the electrocautery device of FIG. 1 with the suction tube assembly in an extended position.

FIG. 1A is a perspective view of one embodiment of the electrocautery device in the retracted configuration, with the suction tube assembly in the retracted position. Electrocautery device 100 includes a housing 102, an electrocautery tip 104, suction tip 118, and one or more vents 106 in the housing. The electrocautery tip 104 and suction tip 118 extend from the distal end 114 of the electrocautery device, while a suction connection 108 extends from the proximal end 116 of the electrocautery device. In practice, a surgeon gripping the electrocautery device can use electrocautery controls 110a and 110b to switch between electrocautery settings and can use button 112 to switch the electrocautery device between the retracted and extended configurations. FIG. 1B shows a perspective view of the electrocautery device in the extended configuration with the suction tube assembly in the extended position. While the device is in the extended configuration, suction tip 118 extends beyond electrocautery tip 104. In the retracted position, the suction tip 118 is retracted behind the electrocautery tip 104, i.e., the electrocautery tip 104 extends beyond suction tip 118.

FIG. 2 is a cross-sectional view of the housing 102 of electrocautery device 100 taken along the cross-section line 2-2 of the device. The housing 102 contains suction cavity 200, which has suction tube suction connection 202 at its proximal end and hard stop 206 at its distal end. Vent passage 212 connects suction cavity 200 to the external environment through vent 106, allowing air to flow between the suction cavity 200 and the environment. The suction cavity is also connected to a suction source through suction connection 108 via suction passage 214. The distal end 114 of the housing 102 includes suction tip cavity 204, which includes locking grooves 210 and piston guides 208, each of which will be detailed below.

FIGS. 3 and 4 are a perspective view of suction tube assembly 300 and a cross-sectional view taken along the longitudinal axis of suction tube assembly 300 respectively. In the retracted configuration, piston 302 is located generally towards the proximal end of the device within suction cavity 200. Suction tube 304 serves as the piston rod to piston 302 and includes the suction tip 118 at its distal end while connecting to a suction source at its proximal end. Relief holes 312 allow continued airflow to the suction source if suction tip 118 becomes blocked during the course of use. The distal end of the piston end of the suction tube assembly ends in piston teeth 310, which interface with the cam teeth 504 of cam 506 as will be described subsequently. Cam guide 314 on the suction tip end of suction tube assembly 300 defines the boundaries of the possible movement range of the cam 506. Cam 506 (not pictured in FIGS. 3 and 4 for clarity) is free to spin on and slide along cam guide 314, but not distal to cam guide 314. Protrusions 308 slide along piston guides 208 of the housing, ensuring smooth movement of the suction tube assembly 300 within the housing 102 over the course of operation.

FIGS. 5A-5E depict the electrocautery device 100 over the course of moving from the retracted configuration to the extended configuration and back. FIG. 5A shows the device beginning in the retracted position to begin the narrative. It should be understood that the device is operational in both the retracted and extended configurations and the order of descriptions given here have no bearing on the relative importance or merits of the device when in each described state. In the retracted configuration, the suction tube assembly is mostly or entirely retracted within the housing, leaving the electrocautery tip 104 extending beyond the suction tip 118. In this configuration, gases, smoke, bodily fluids, and possibly small solids can freely flow from the suction tip 118 to the suction source through suction tube suction connection 202. Similarly, air is free to flow into the housing 102 and to the suction source through vent 106, vent passage 212, suction passage 214, and suction connection 108. Due to the spring force of proximal spring 502, suction tube assembly 300 and piston 302 rest at the proximal end of the suction cavity in the retracted state. Distal spring 508 rests at the distal end 114 of the device undisturbed by cam 506. In this configuration, the electrocautery tip 104 is the distal most point of the device; the inventors have contemplated that this would be the preferred configuration for actual cutting and cauterizing use, but a user is free to cut and cauterize in any configuration based on their individual preferences. Thus, the current disclosure is not so limited.

To switch from the retracted configuration to the extended configuration, the user depresses button 112, which blocks vent passage 212, effectively cutting off communication between vent 106 and the rest of the interior of the device. In this embodiment, depressing button 112 closes a diaphragm valve for as long as the button is depressed. However, any system for reversibly or temporarily obstructing airflow between the vent 106 and suction cavity 200, manual or controller operated, can be utilized. With the vent 106 blocked from communication with the rest of the device, the suction source connected via suction connection 108 evacuates an effective amount of the remaining air in the housing, producing a vacuum in suction cavity 200 distal to piston 302. This vacuum produces a vacuum force on the piston 302, overcoming the spring force from proximal spring 502, causing the piston 302 and consequently the entire suction tube assembly 300 to slide distally relative to the housing 102. As the piston portion of suction tube assembly 300 slides distally, it encounters and pushes cam 506 distally, causing the cam to depress distal spring 508. When the cam stops sliding distally, as will be described subsequently, the piston causes the cam to rotate relative to the longitudinal axis of the suction tube assembly 300. The suction tube assembly 300 slides distally until piston 302 is blocked by hard stop 206, leaving the suction tip 118 extended beyond electrocautery tip 104. The device remains in this hyperextended configuration depicted in FIG. 5B, with the suction tube assembly 300 in a hyperextended position, until the user releases the obstruction of vent passage 212.

When the user releases button 112, free communication is again established between the external environment and suction cavity 200, alleviating the vacuum. Without the vacuum force acting on piston 302, the spring force from proximal spring 502 causes the piston 302 and the entire suction tube assembly 300 to begin sliding proximally. In its rotated state, cam 506 becomes caught in locking grooves 210 as the suction tube assembly 300 slides proximally, locking the suction tube assembly 300 in the extended position shown in FIG. 5C. When locked in the extended position, the suction tube assembly 300 cannot be pushed further into the housing of the device without unlocking the device. As a result, a user can use the suction tip 118 to dissect during surgery, or can otherwise apply axial forces to the suction tip 118 without having to worry about the suction tube assembly 300 retracting.

When the user desires to unlock and retract the suction tube assembly 300, the user simply depresses button 112 again. As seen in FIG. 5D, depressing the button 112 blocks vent passage 212, thereby blocking connection between the external environment and the suction cavity 200. This once again allows the suction source to remove an effective amount of the air from the interior of the housing 102 through suction connection 108, producing a vacuum in the suction cavity proximal to piston 302. This causes piston 302 to again slide proximally, shifting the entire suction tube assembly 300 proximally, sliding the cam 506 distally out of locking grooves 210. When the cam 506 makes contact with distal spring 508, it rotates again relative to the longitudinal axis of the suction tube assembly 300, rotating the cam teeth 504 out of alignment with the locking grooves 210. The suction tube assembly 300 once again comes to rest in the hyperextended configuration as long as the vent passage 212 remains blocked.

When the user releases the obstruction to vent passage 212, the vacuum is again alleviated, allowing proximal spring 502 to force piston 302 and thus suction tube assembly 300, to slide proximally. Since the cam 506 was rotated out of alignment with locking grooves 210, the cam 506 freely slides past the locking grooves 210, allowing the entire suction tube assembly 300 to return to the retracted position with piston 302 at the proximal end of the suction cavity 200 as seen in FIG. 5E (which is identical to FIG. 5A).

As should be appreciated by one of skill in the art, although the depicted embodiments all have each component depicted in substantially the same location relative to each other, the described device does not have to be arranged as shown and its components do not have to be shaped as shown. For instance, the housing could be of any shape that could be reasonably gripped by a user. In some embodiments, the housing has an offset end that the electrocautery tip extends from such that the electrocautery tip extends longitudinally from a height above or below the rest of the housing. In some embodiments, the electrocautery tip is attached to a section of the housing that is capable of rotating relative to the rest of the housing such that the electrocautery tip can pitch and/or yaw relative to the majority of the housing. In other embodiments, the proximal end of the device can swivel freely so that the user is not significantly restrained by particularly thick suction tubing required for some surgical applications. The buttons could be in different locations on the housing and do not have to be constrained to the depicted position in the depicted order. Similarly, in the depicted embodiment, the vents are located close to the distal end to assist with smoke evacuation, but the vents do not necessarily have to be located as depicted and can be located anywhere on the housing as long as an air communication between the vents and the suction cavity can be established and blocked.

Figure 6A:
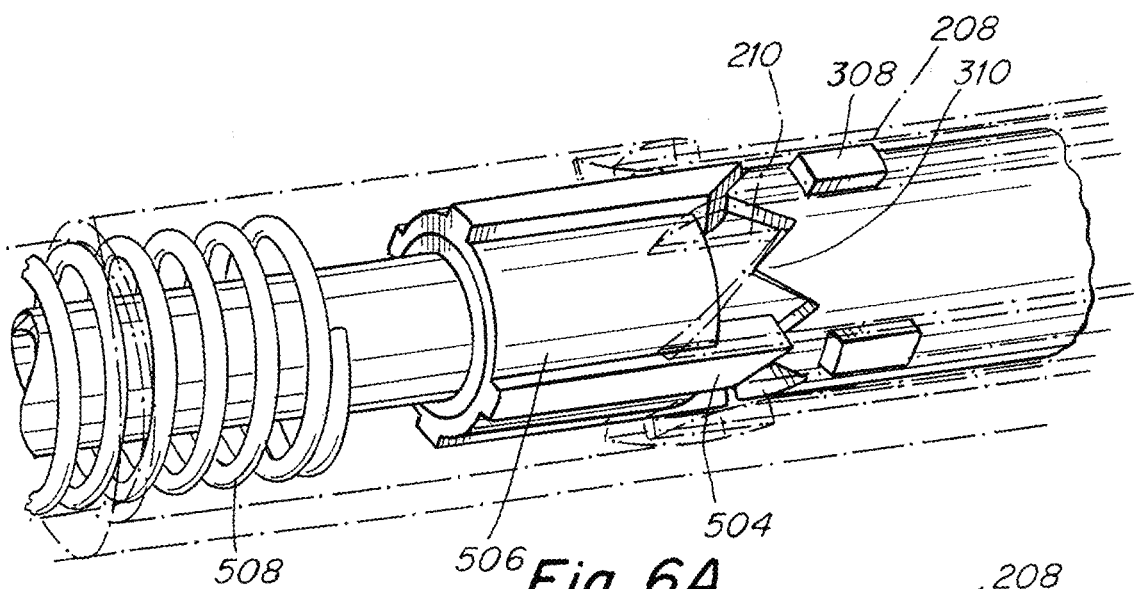
FIG. 6A is a close-up, top, right side view of a cam and a piston of the suction tube assembly in the retracted position, with the housing of the device shown in phantom.
Figure 6B:
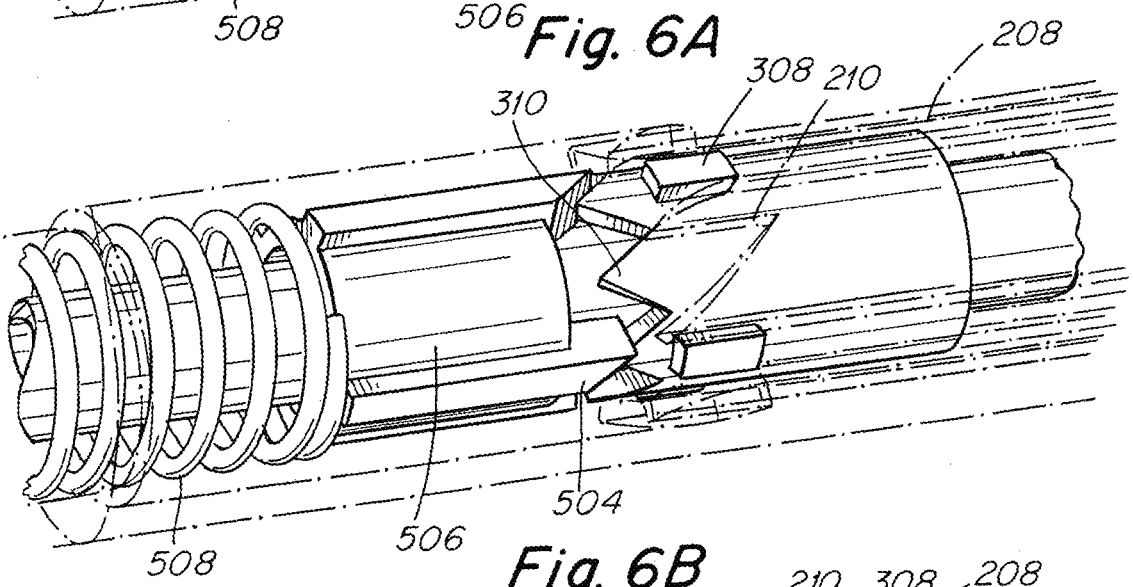
FIG. 6B is a close-up, top, right side view of the cam and the piston of the suction tube assembly during transition from the retracted position to the extended position, with the housing of the device shown in phantom.
Figure 6C:
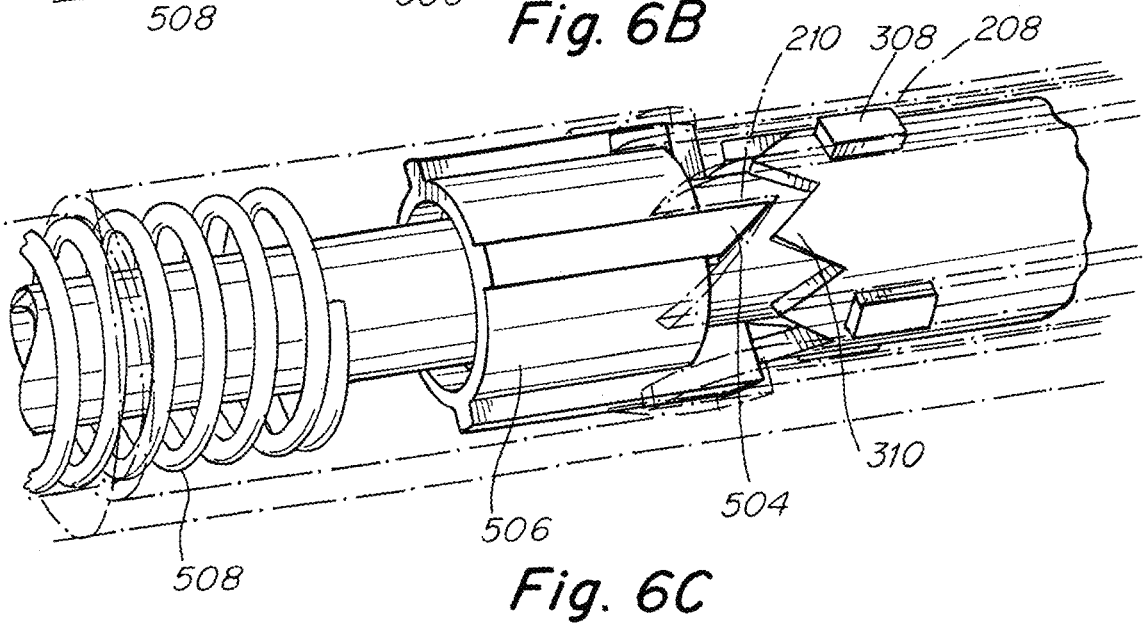
FIG. 6C is a close-up, top, right side view of the cam and the piston of the suction tube assembly locked in the extended position, with the housing of the device shown in phantom.

FIGS. 6A-6C and FIGS. 7A-7C are a close up view of the "click-lock" mechanism responsible for locking and unlocking the suction tube assembly 300 as previously described. FIG. 6A shows the piston end of the suction tube assembly 300 sliding distally during the transition from the retracted position to the extended position. Initially, as the piston slides, the cam 506 slides forward as well until cam 506 encounters spring 508. At that point, the piston continues sliding distally relative to the cam. As the piston end slides, protrusions 308 move along piston guides 208. As seen in FIG. 6B, when the piston teeth 310 encounter the cam 506, a first "click" is heard and/or felt, and the cam is pushed distally against spring 508 along with the suction tube assembly 300. When the cam 506 encounters distal spring 508, the sloped edges of the piston teeth 510 push against the sloped edges of cam teeth 504, causing the cam to rotate into alignment with locking grooves 210. When the vacuum is alleviated, as seen in FIG. 6C, spring 508 forces the entire suction tube assembly 300 to slide proximally, forcing cam 506 to slide proximally due to cam 506 being constrained to cam guide 314. As the suction tube assembly 300 slides proximally, the cam teeth 504 engage with locking grooves 210, causing a second "click" to be heard, and locking the suction tube assembly in the extended position.

Figure 7A:
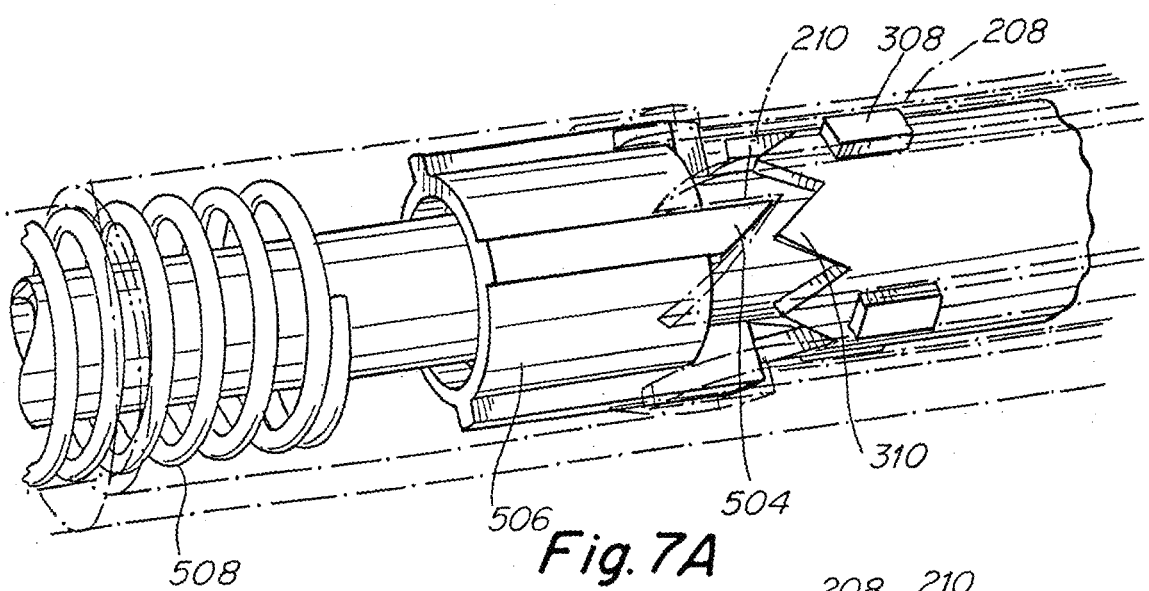
FIG. 7A is a close-up, top, right side view of the cam and a piston of the suction tube assembly locked in the extended position, with the housing of the device shown in phantom.
Figure 7B:
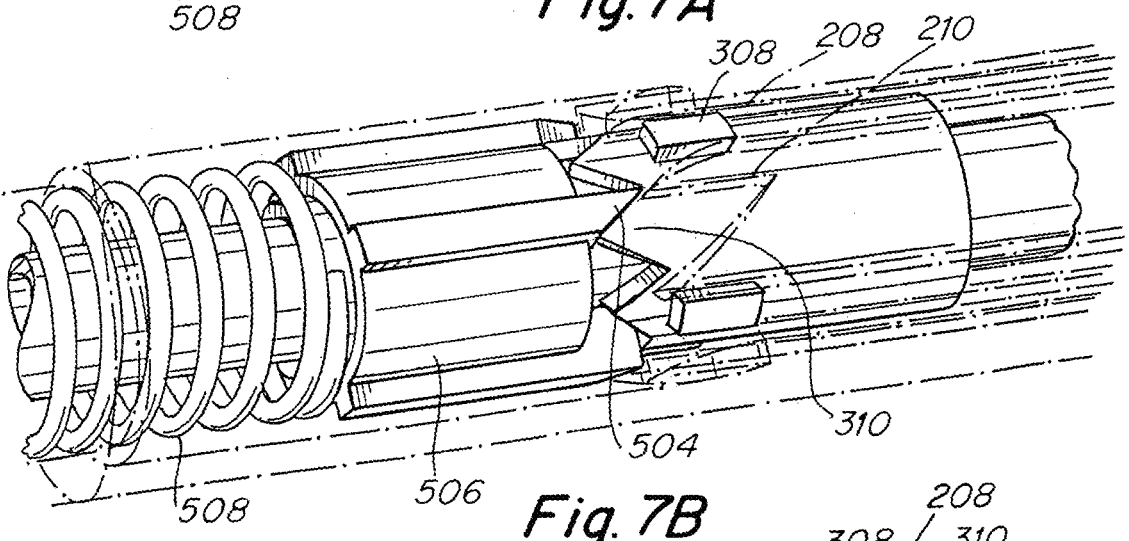
FIG. 7B is a close-up, top, right side view the cam and a piston of the suction tube assembly during transition from the extended position to the retracted position, with the housing of the device shown in phantom.
Figure 7C:
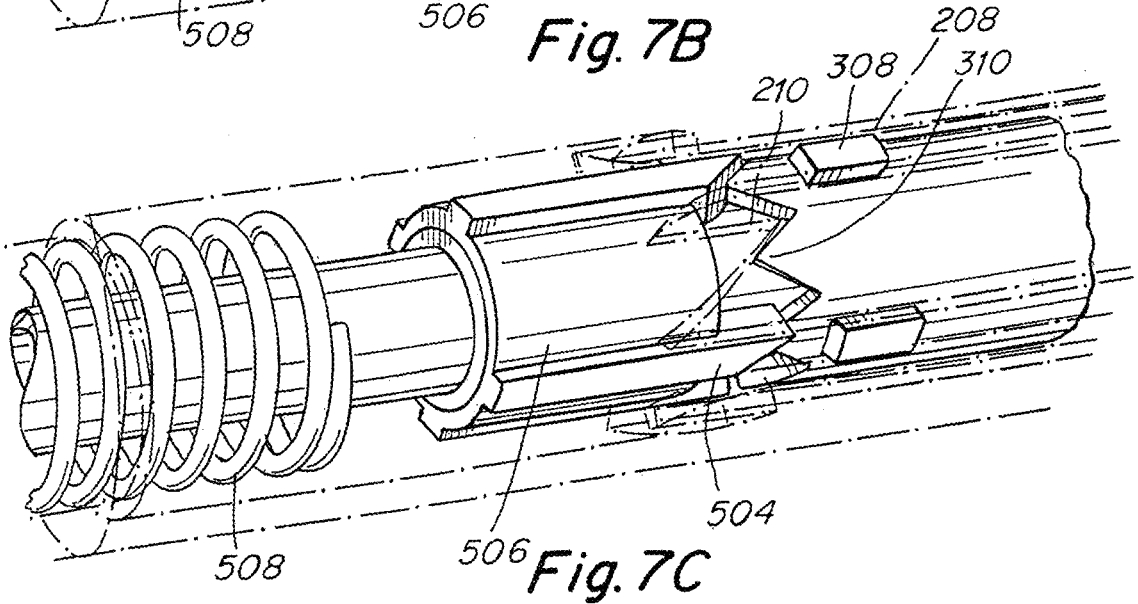
FIG. 7C is a close-up, top, right side view of the cam and a piston of the suction tube assembly in the retracted position, with the housing of the device shown in phantom.

FIG. 7A shows the piston end of the suction tube assembly 300 approaching cam 506 during the transition between the extended and retracted positions. As the piston end of suction tube assembly slides distally, it encounters cam 506 in its extended configuration position within locking grooves 210, producing a single "click." The piston end pushes cam 506 out of the locking grooves until the cam 506 encounters distal spring 508. As seen in FIG. 7B, once again, the sloped edges of the piston teeth 310 interact with the cam teeth 504 when the cam is pressed against the distal spring 508, causing the cam 506 to rotate the cam teeth 504 out of alignment with locking grooves 210. As seen in FIG. 7C, when the vacuum is alleviated, the suction tube assembly 300 begins sliding proximally, forcing cam 506 to slide proximally due to the cam 506 being constrained to cam guide 314 on the suction tube assembly. With the cam teeth 504 out of alignment with the locking grooves 210, the cam freely slides proximally past the locking grooves 210, allowing the entire suction tube assembly to return to the retracted configuration.

As should be readily appreciated, the deployment and the retraction of the suction tube assembly 300 rely entirely on the suction source. No motors or manual movement of the suction tube assembly is necessary. However, an additional feature of the electrocautery device 100 is that if the suction source were to fail for whatever reason, if the user desired to retract the suction tube (or extend it for whatever reason while the suction source is not working), the user can simply physically pull the suction tip distally. Pulling the suction tip distally mimics the effect of apply a vacuum to the distal end of the piston 302, forcing the entire suction tube assembly 300 to slide distally overcoming the spring force from proximal spring 502. Just as if the vacuum was being generated normally, as the cam 506 slides forward, encounters the distal spring 508 and is rotated by the piston teeth 310 pressing against cam teeth 504. Thus, a user can simply pull the suction tip 118 and cause the cam 506 to rotate in and out of alignment with locking grooves 210. When the user releases the suction tip 118, the entire suction tube assembly 300 begins sliding proximally due to the spring force of proximal spring 502, causing the cam 506 to either become trapped in locking grooves 210 or slide freely past locking grooves 210 depending on what configuration the suction tube assembly 300 was in previously. As such, a user can manually place the electrocautery device in its extended or retracted configurations by simply pulling on and releasing the suction tip if the suction source fails.

While the depicted embodiments of the "click-lock" mechanism are depicted as relying on proximal and distal helical springs, it should be appreciated that any sufficiently rigid elastic structure can be used as long as the structure is strong enough to remain in the elastic region of stress/strain during deformation when being compressed by the piston or cam. Additionally, the proximal spring could be any elastic structure that produces a spring force less than the applied vacuum force. The inventors have contemplated other types of springs, compressible foams, and compressible plastics, but the current application is not limited as such.

Figure 8A:
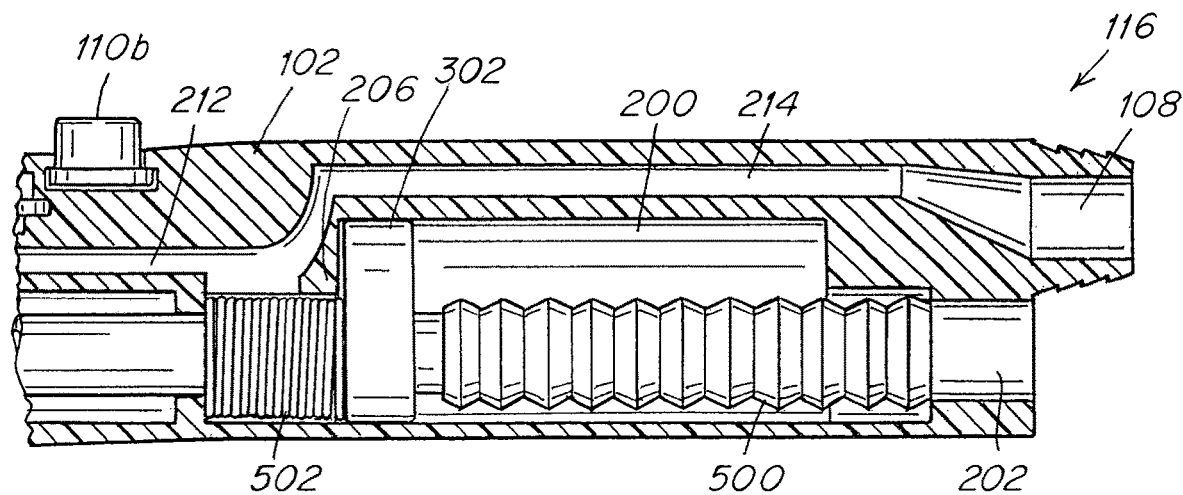
FIG. 8A is a close-up, right side view of flexible tubing connecting the suction tube assembly to a suction source with the suction tube assembly in the extended position.
Figure 8B:
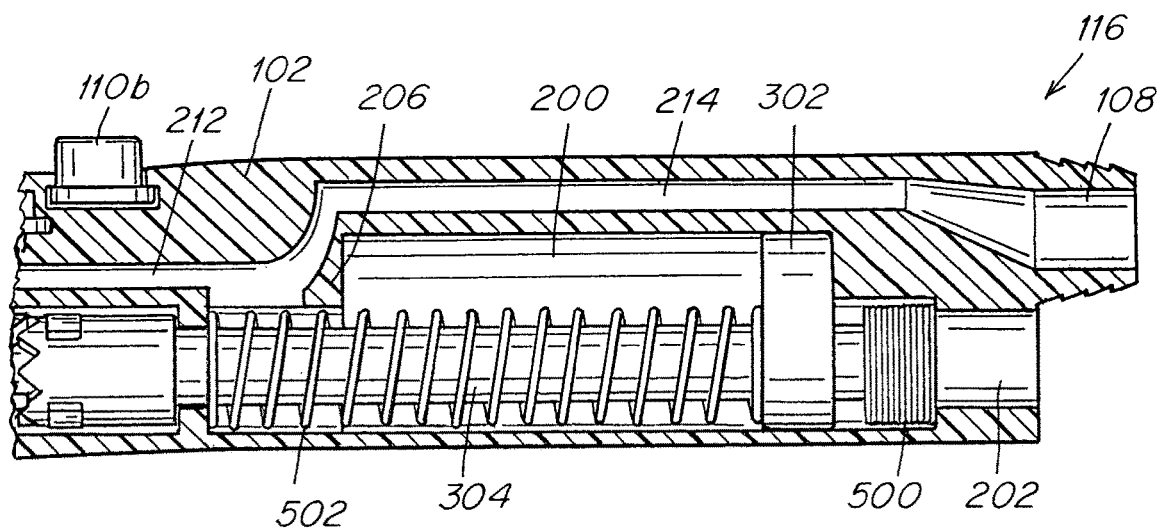
FIG. 8B is a close-up, right side view of flexible tubing connecting the suction tube assembly to a suction source with the suction tube assembly in the retracted position.

In some embodiments of the electrocautery device, the proximal end of the suction tube assembly is connected to suction tube suction connection 202 via a flexible bellows-like tubing with concertinaed sides that can expand when the suction tube assembly extends, and contract when the suction tube assembly retracts, without compromising isolated flow from the suction tube assembly to the suction source. FIG. 8A shows the suction tube assembly 300 in the extended position with the piston against hard stop 206 and the flexible bellows tubing 500 expanded to accommodate the suction tube assembly's position. FIG. 8B shows the suction tube assembly 300 in the retracted position with the flexible bellows tubing 500 contracted to again accommodate the position of the suction tube assembly. As one of skill in the art would appreciate, other arrangements are possible, including a coiled telephone cable like arrangement, or a telescoping arrangement. The current application is not limited to the depicted embodiment or the described alternatives, any connection type that is capable of expanding and contract reliably without compromising flow could be used.

Some embodiments of the flexible bellows tubing include a spring built into the material of the bellows such that the bellows serves as the spring that returns the piston to the retracted position. In these embodiments, instead of, or in addition to, a separate proximal spring that is compressed by the piston as it slides distally, the bellows itself has a spring constant associated with it and asserts a spring force biasing the piston proximally when the piston is distal to the retracted position. When the vacuum pulls the piston distally, the bellows expands against the spring force as the piston slides. When the vacuum is alleviated, the spring force from the bellows pulls the piston back to the retracted position. Other arrangements besides the bellows explicitly containing a spring are contemplated, for instance, the bellows could be made of an elastic material such that the bellows material itself acts as an extension spring.

Figure 9A:
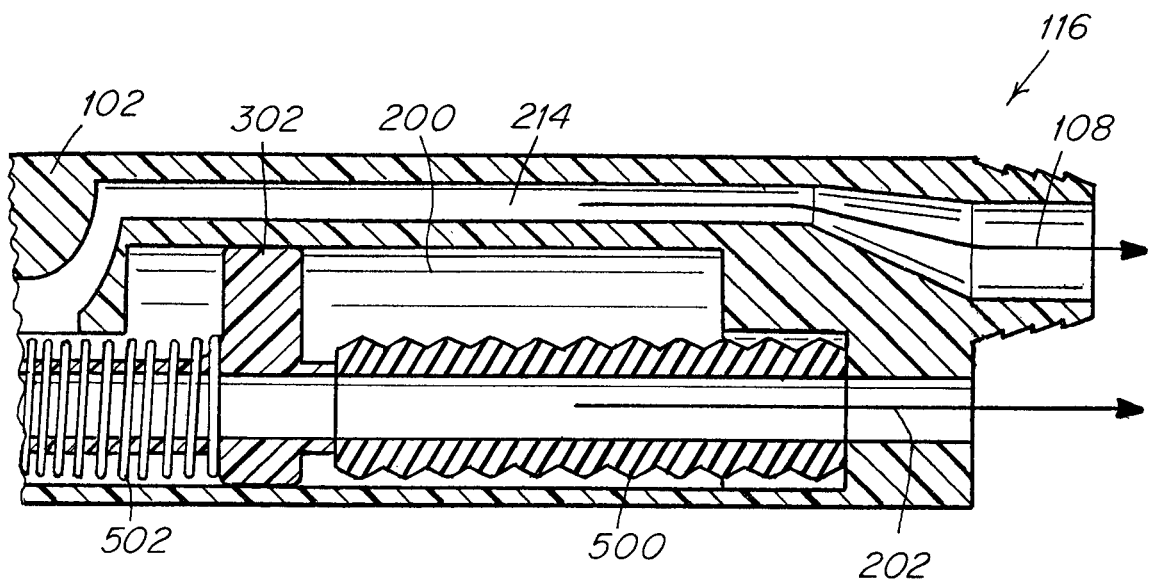
FIG. 9A is a close-up, right side cross-sectional view of one embodiment of the electrocautery device with separate suction sources for air and fluid flow.
Figure 9B:
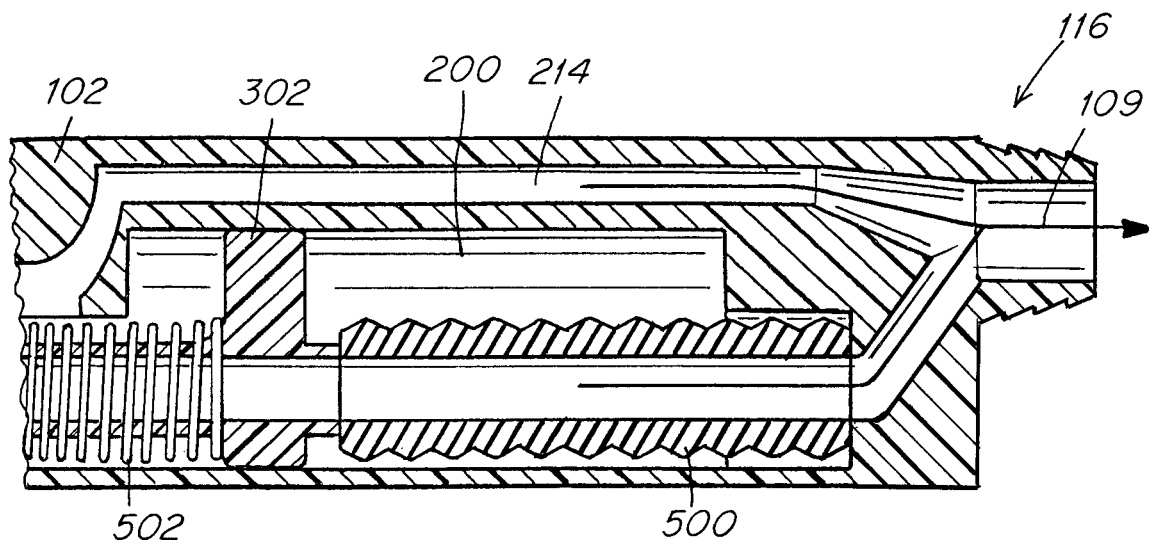
FIG. 9B is a close-up, right side cross-sectional view of one embodiment of the electrocautery device with a single suction source for air and fluid flow.

While the described embodiments have relied on different suction sources connected to suction connection 108 and suction tube suction connection 202, embodiments that rely on a single suction source are also contemplated. FIG. 9A shows the dual suction source arrangement of the previously described embodiments. Flow through suction connection 108 is designed for air flow through the vent, while flow through suction tube suction connection 202 accommodates anything that the suction tip vacuums up from the working environment. FIG. 9B depicts an embodiment that relies on one single suction connection 109 that provides the suction for both the vent and the suction tip. Other embodiments with more than two suction sources are also contemplated.

Figure 10A:
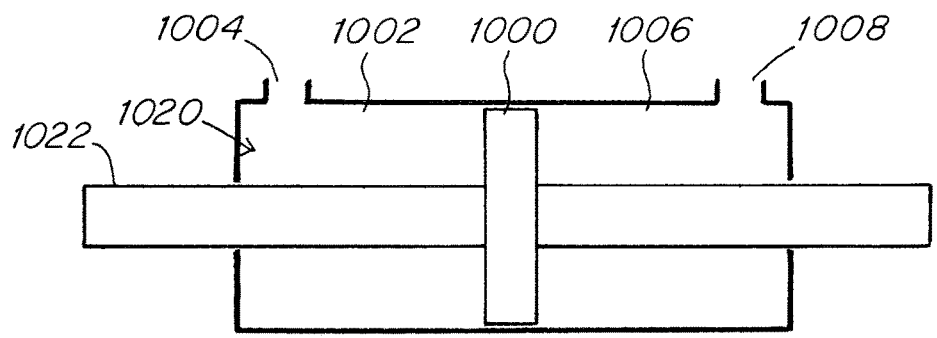
FIG. 10A is a schematic representation of a suction cavity and the piston in between the extended position and retracted position according to one embodiment of the electrocautery device.
Figure 10B:
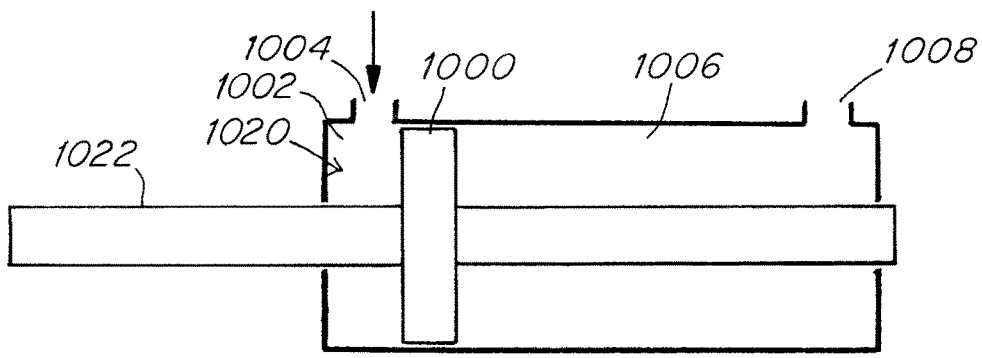
FIG. 10B is a schematic representation of the suction cavity and piston in the retracted position according to the embodiment of FIG. 10A.
Figure 10C:
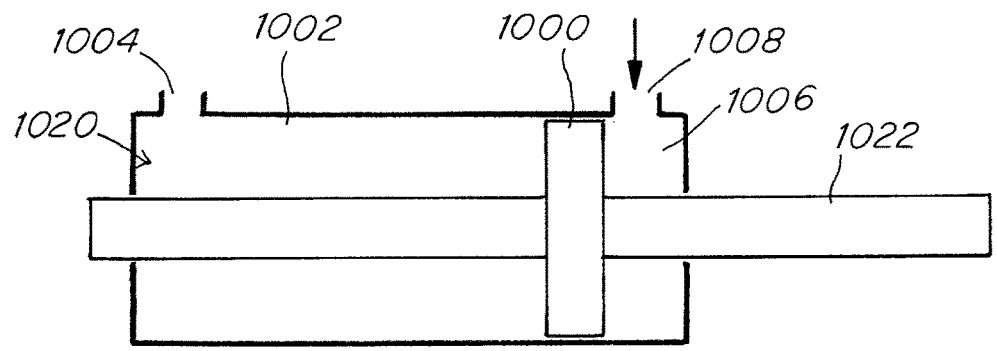
FIG. 10C is a schematic representation of the suction cavity and piston in the extended position according to the embodiment of FIG. 10A.

The inventors have contemplated that a suction cavity divided into proximal and distal suction regions separated by a piston could be used to retract and extend the suction tube assembly using a suction source alone. FIGS. 10A-10C are schematic representations of said dual suction region mechanism. Suction cavity 1020 is divided into a proximal suction region 1002 and a distal suction region 1006 by piston 1000 attached to suction tube 1022. Proximal hole 1004 forms a connection between a suction source and the proximal suction region 1002, and distal hole 1008 forms a connection between a suction source and the distal suction region 1006. As seen in FIG. 10B, when the suction source is diverted to the proximal hole 1004, a vacuum is formed in the proximal suction region 1002. The piston 1000 is drawn towards the vacuum, causing the piston 1000 and the suction tube 1022 to slide distally, shrinking the proximal suction region 1002 and growing the distal suction region 1006. Similarly, as seen in FIG. 10C, when the suction is diverted through distal hole 1008, a vacuum is formed in the distal suction region 1006. Thus, the piston 1000 and suction tube 1022 slide distally, shrinking the distal suction region 1006 and growing the proximal suction region 1002.

In some of the subsequent embodiments, a simple piston and suction tube as a piston rod arrangement without additional complexities is depicted. One of skill in the art should understand that the more complicated suction tube assembly including the click-lock mechanism previously described can be used in these embodiments as well.

Figure 11:
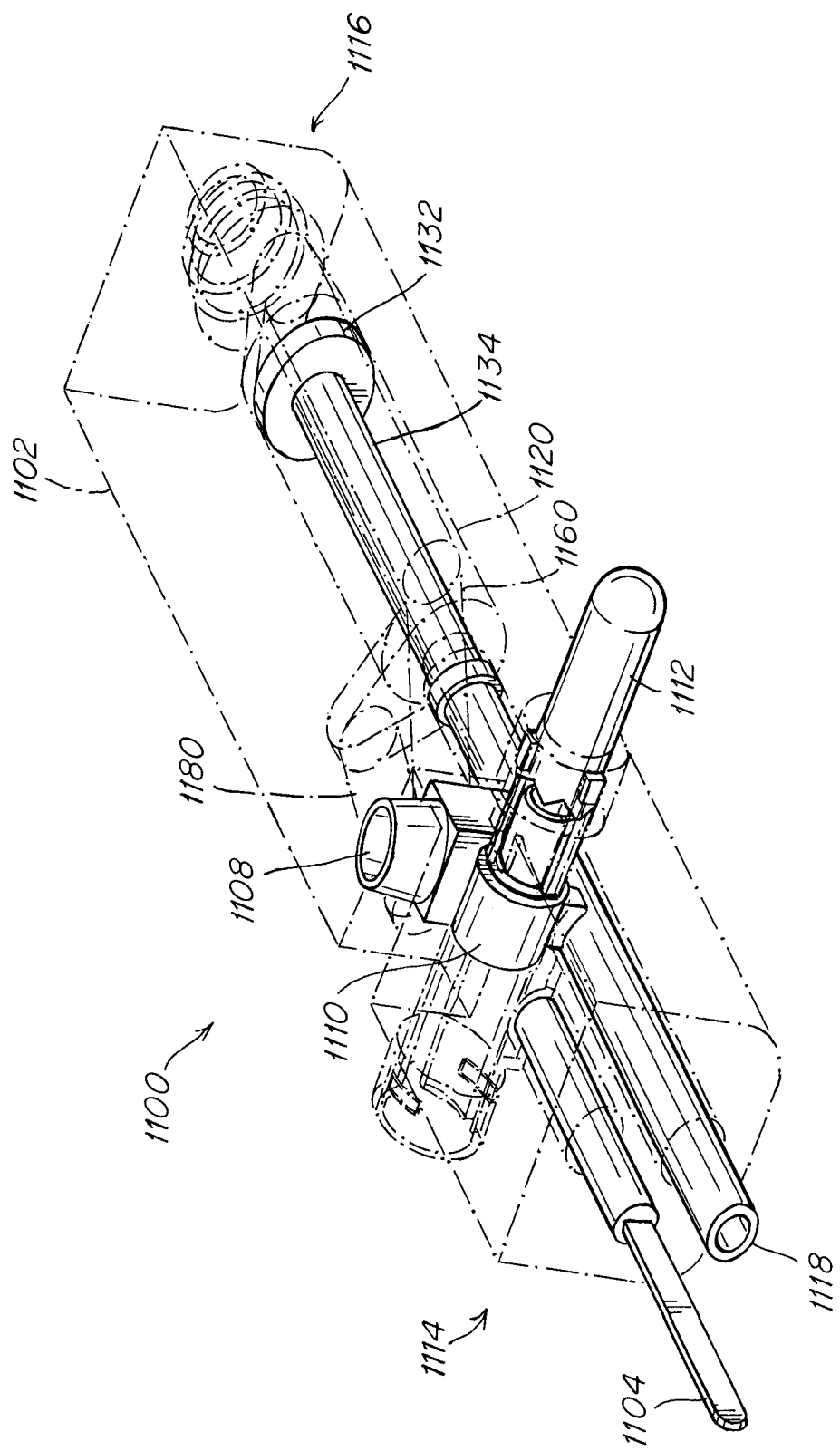
FIG. 11 is a top, right side perspective view of the electrocautery device according to one embodiment, with the housing of the device shown in phantom.
Figure 12A:
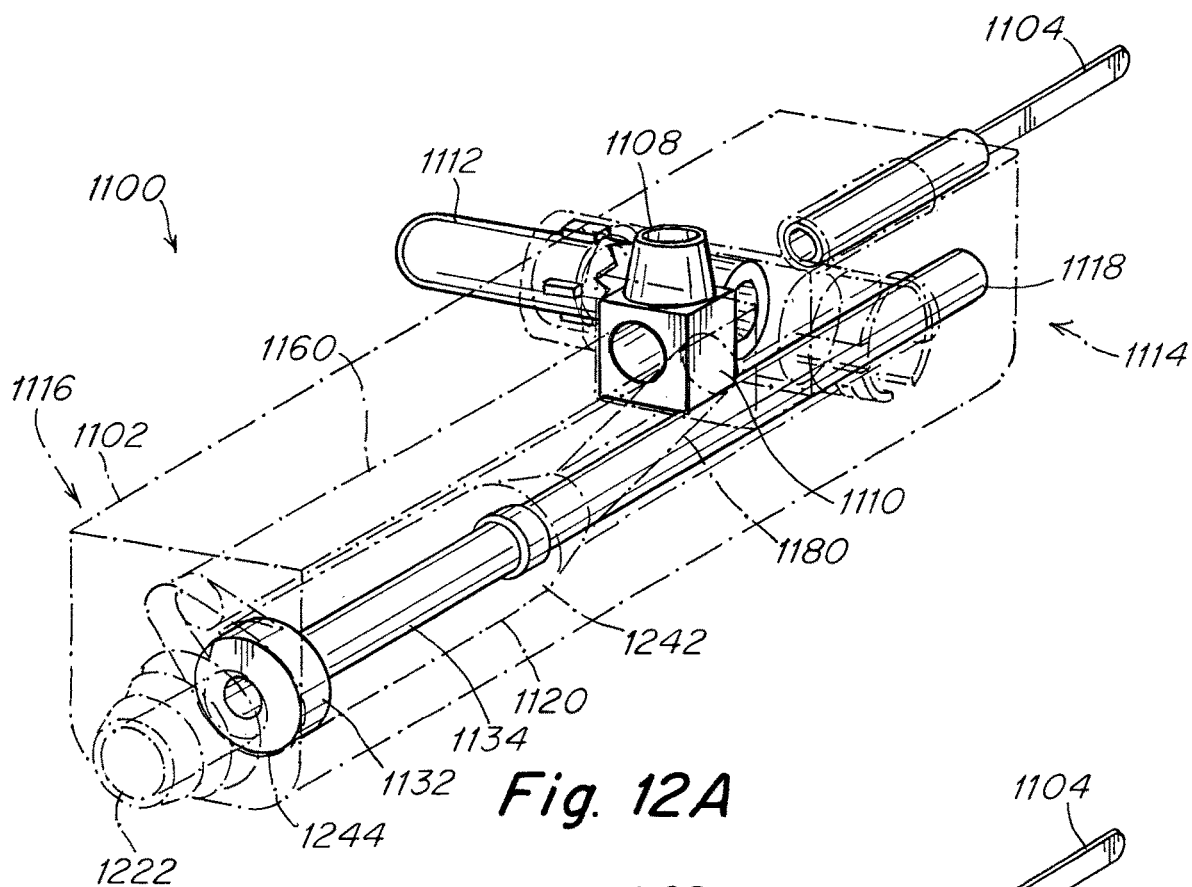
FIG. 12A is a top, left side, rear perspective view of the electrocautery device of FIG. 11 with the suction tube assembly in the retracted position.
Figure 12B:
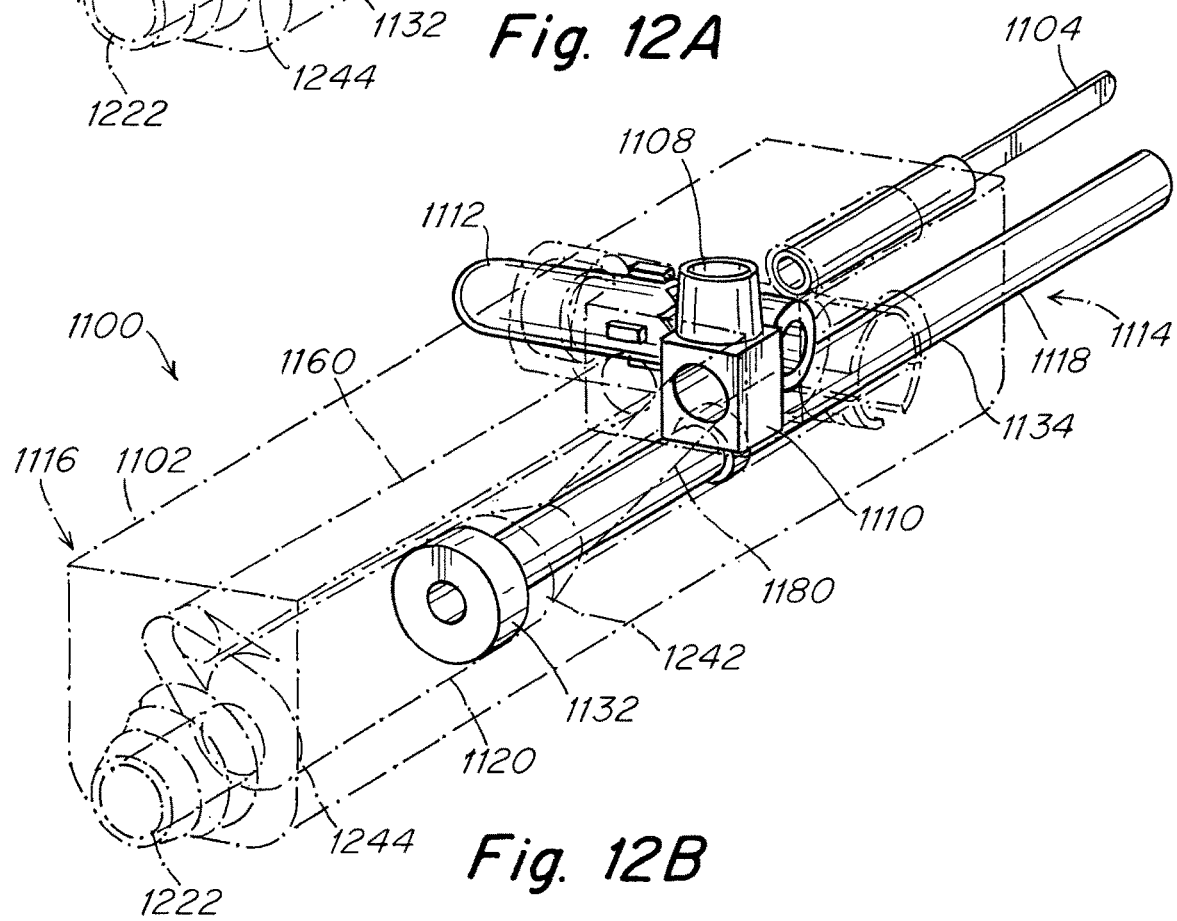
FIG. 12B is a top, left side, rear perspective view of the electrocautery device of FIG. 11 with the suction tube assembly in the extended position.
Figure 13:
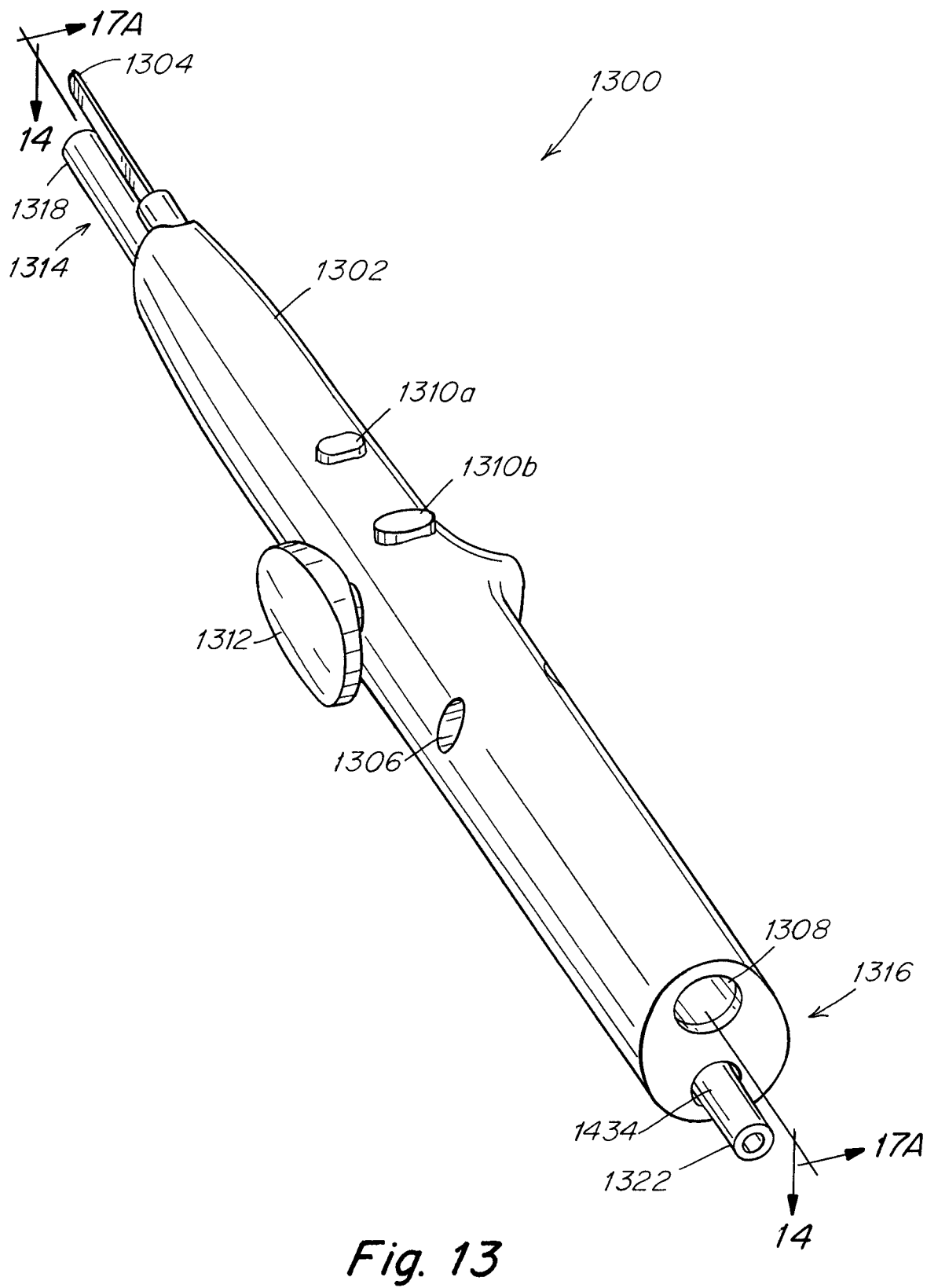
FIG. 13 is a top, right side, rear perspective view of the electrocautery device according to one embodiment.

FIGS. 11, 12A, and 12B are perspective views of one embodiment of the electrocautery device 1100 that relies on the dual suction region mechanism described previously. In this embodiment, electrocautery tip 1104 and suction tip 1118 protrude from the distal end 1114 of the device. Piston 1132 is mechanically contiguous with suction tube 1134 and divides suction cavity 1120 into proximal suction region 1244 and distal suction region 1242. Suction tube 1134 is connected to a suction source via suction connection 1222. Spring-loaded button 1112 controls the position of linear diverter 1110, which is connected to the suction source via suction connection 1108.

When the button 1112 is undepressed as seen in FIG. 12A, the linear diverter 1110 forms a connection between the suction source and the proximal suction channel 1160. The proximal suction channel 1160 connects to the proximal suction region 1244. Thus, when air is drawn from the proximal suction channel 1160, a vacuum is formed in the proximal suction region 1244, forcing the piston 1132 and suction tube 1134 to slide proximally. This causes the suction tube 1134 to retract towards proximal end 1116, retracting the suction tip 1118 and placing the electrocautery device 1100 in the retracted configuration.

As seen in FIG. 12B, when button 1112 is depressed, the linear diverter forms a connection between the suction source and distal suction channel 1180. The distal suction channel 1180 connects to distal side of the suction cavity 1120. Thus, when air is drawn from the distal suction channel 1180, a vacuum is formed in the distal suction region 1242. The piston 1132 is drawn towards the vacuum, sliding distally until it reaches the end of the suction cavity 1120, extending the suction tube out the distal end 1114 of the device 1100 and placing the electrocautery device 1100 in the extended configuration.

One of skill in the art should understand that the depressed and undepressed positions of the button 1112 are used to describe possible binary configurations of any possible generic switching mechanism that can control a linear diverter.

FIGS. 13-17C are another embodiment of the electrocautery device that relies on the dual suction region mechanism. Electrocautery device 1300 has an electrocautery tip 1304 and suction tip 1318 protruding from its distal end 1314. The proximal end 1316 of the electrocautery device 1300 includes suction connection 1308 and the proximal end of suction tube 1434 includes suction tube suction connection 1322. Electrocautery buttons 1310a and 1310b, as well as button 1312 and vent 1306 are located on the housing 1302. As seen in FIGS. 14-15, suction cavity 1420 inside housing 1302 is a semi-lunar structure with distal hole 1424 and proximal hole 1426 spaced at lateral and longitudinal opposing ends. Piston 1532 is similarly semi-lunar shaped to divide suction cavity 1420 into a distal suction region 1502 and proximal suction region 1506.

Figure 16A:
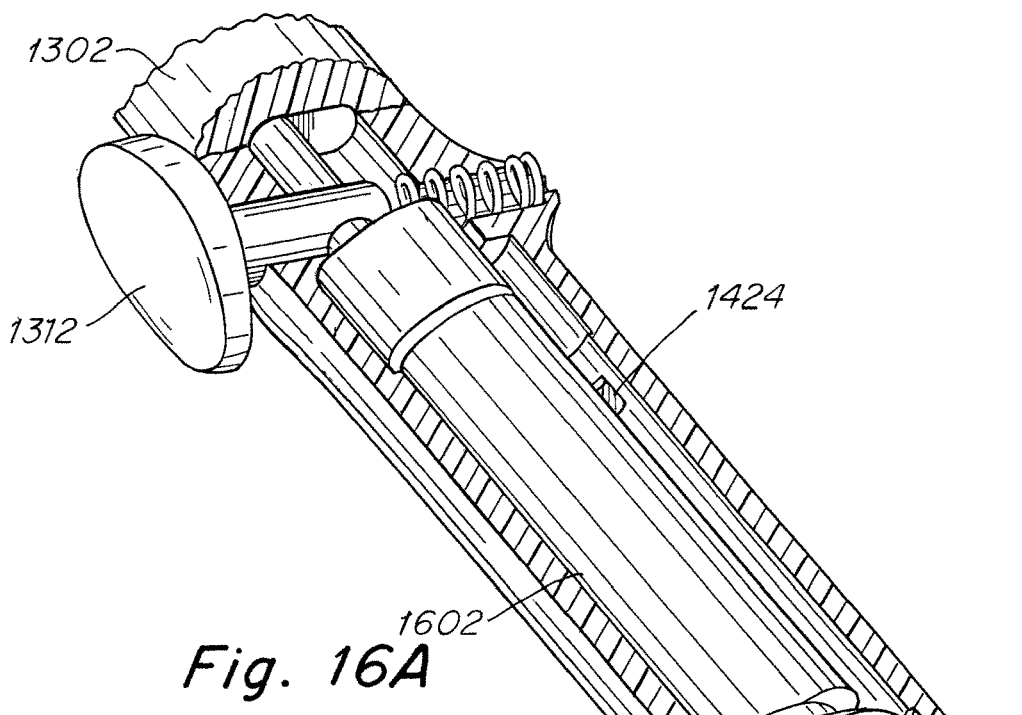
FIG. 16A is a top, right side, rear cross-sectional view of the electrocautery device of FIG. 13 in a retracting configuration.
Figure 16B:
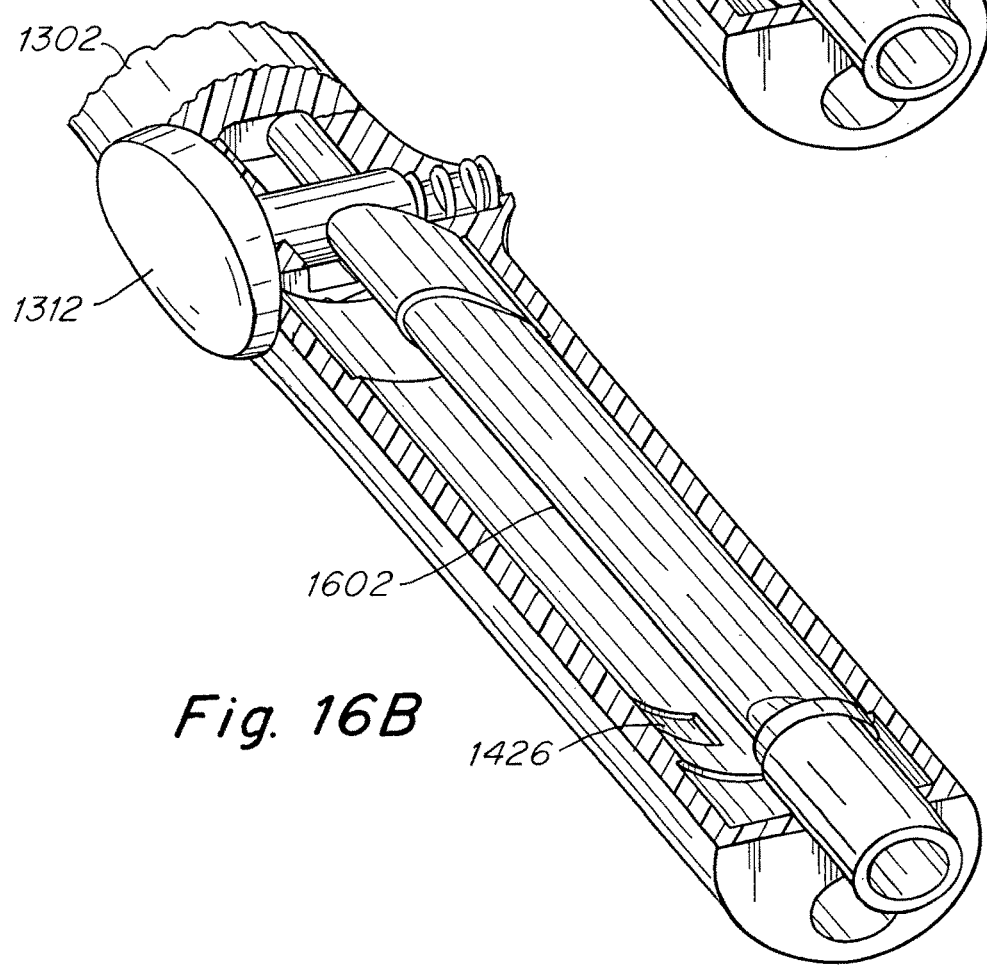
FIG. 16B is a top, right side, rear cross-sectional view of the electrocautery device of FIG. 13 in an extending configuration.

Turning to FIGS. 16A and 16B, when a user actuates spring-loaded button 1312, suction channel 1602, which directly contacts suction cavity 1420, is "swung" between lateral sides of the electrocautery device 1300. Suction channel 1602 has holes that map to proximal and distal holes 1424 and 1426. In the "retract" state of button 1312, suction channel 1602 rests over proximal hole 1426, allowing distal hole 1424 to communicate with the environment via vent 1306. By resting over proximal hole 1426, the corresponding hole in the suction channel 1602 rests directly over proximal hole 1426, allowing communication between the suction source and the proximal suction region 1506. The alignment creates a vacuum in the proximal suction region 1506, forcing the piston 1532 and suction tube 1434 to slide proximally, retracting the suction tube and placing electrocautery device 1300 in the retracted configuration. In the "extend" state of button 1312, suction channel 1602 rests over distal hole 1424, allowing proximal hole 1426 to exchange with the environment via vent 1306. In this state, distal hole 1424 aligns with the corresponding hole in the suction channel 1602, creating a vacuum in the distal suction region 1502. As piston 1532 slides towards the vacuum, suction tube 1434 is towards the distal end 1314 of electrocautery device 1300, placing the device in the extended configuration.

FIGS. 17A-17C represent an embodiment of electrocautery device 1300 including the click-lock mechanism. In this embodiment, suction tube assembly 1736 includes a piston end extending from suction tube suction connection 1322 to piston teeth 1730, and a suction tip end extending from suction tip 1318 to cam 1756. As seen in FIG. 17A, when the electrocautery device 1300 is in the retracted configuration, piston 1532 begins essentially at proximal hole 1426. When the user actuates button 1312, producing a vacuum in the distal suction region 1502, the piston 1532 and suction tube assembly 1736 begin sliding towards distal hole 1424 with protrusions 1738 sliding along piston guides in the housing 1302. As the suction tube assembly slides distally, as seen in FIG. 17B, the cam 1756 encounters distal spring 1758, causing the cam to rotate into alignment with locking grooves 1721 due to the interaction of the sloped cam teeth and piston teeth 1731. When the user releases button 1312, the suction channel 1602 swings, aligning with the proximal hole 1426. The vacuum generated in the proximal suction region then draws the piston and suction tube assembly proximally, causing the cam to become trapped in the locking grooves 1721, locking the suction tube assembly 1736 in the extended configuration seen in FIG. 17C.

To retract the suction tube assembly 1736, the user simply actuates button 1312 again, creating the vacuum in the distal suction region 1502 and drawing the piston and suction tube assembly distally. The piston teeth push the cam 1756 distally out of the locking grooves 1721, causing the cam to rotate out of alignment with the locking grooves when the cam encounters distal spring 1758. The device remains in this hyperextended configuration until the user releases button 1312, creating the vacuum in the proximal suction region 1506 again, drawing the piston and suction tube assembly proximally. The cam slides proximally, clearing the locking grooves and allowing the entire suction tube assembly to return to its retracted position.

Figure 18:
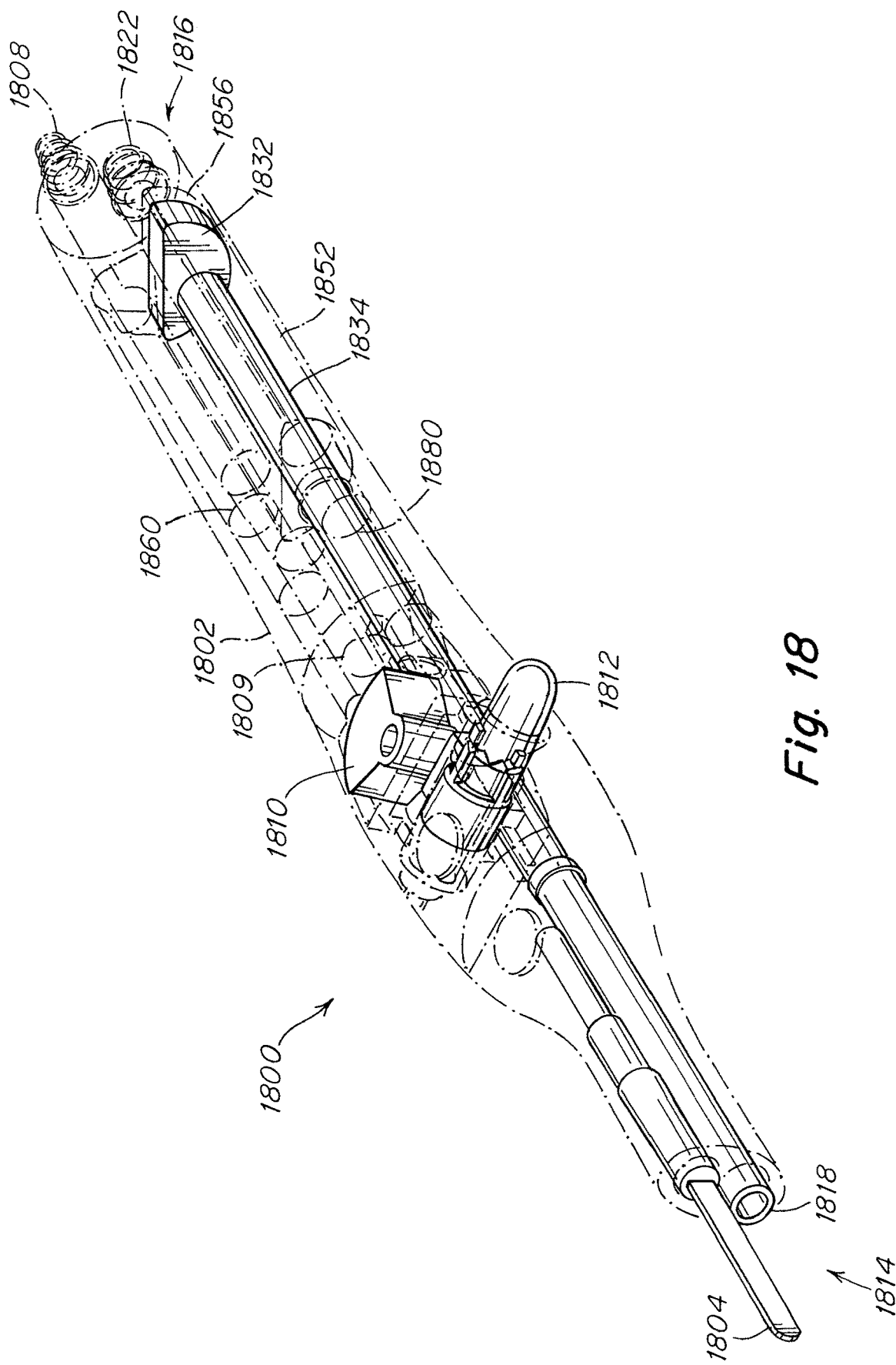
FIG. 18 is a top, front, right side perspective view of the electrocautery device according to one embodiment with the housing shown in phantom.
Figure 19A:
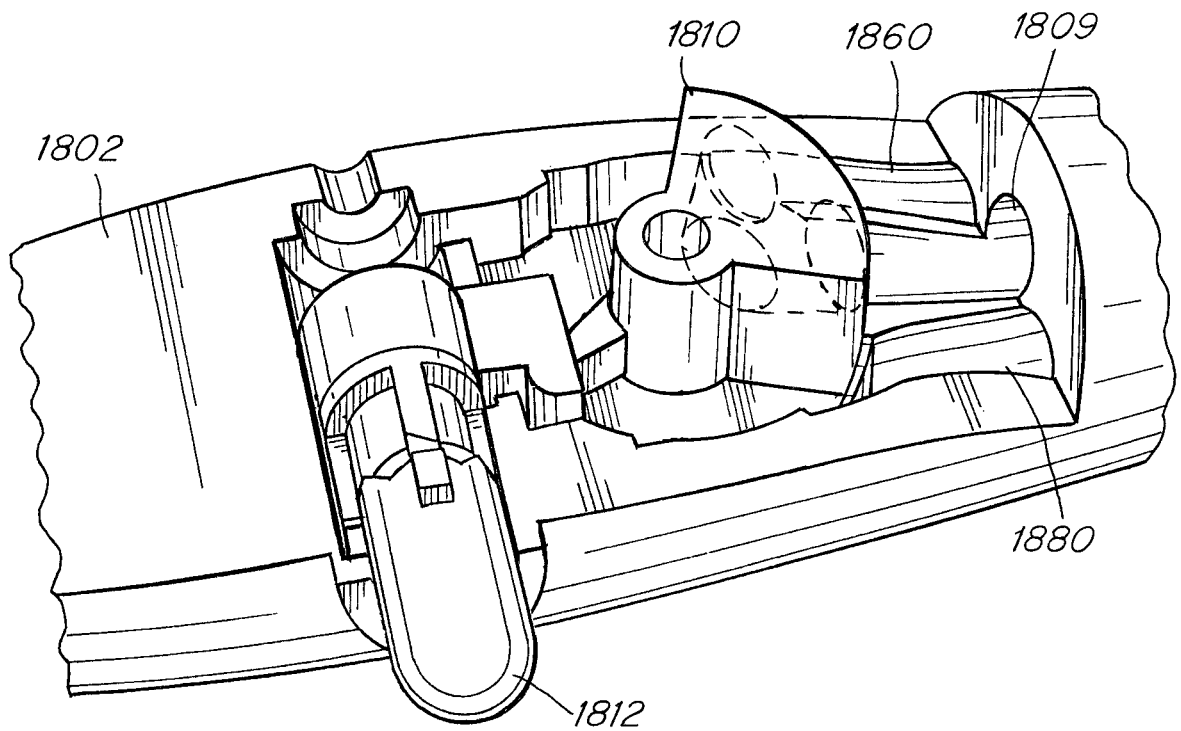
FIG. 19A is a close-up, perspective view of a rotating toggle of the electrocautery device of FIG. 18 in a retracting configuration.
Figure 19B:
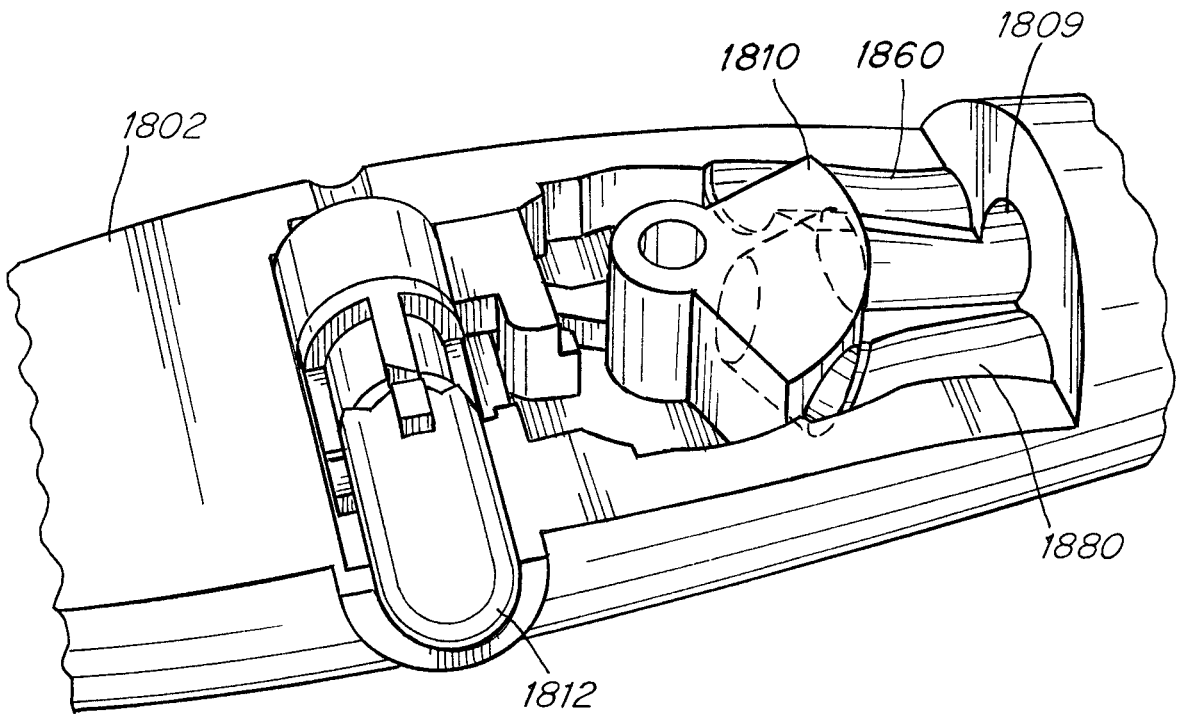
FIG. 19B is a close-up, perspective view of a rotating toggle of the electrocautery device of FIG. 18 in an extending configuration.

FIG. 18-19B show another embodiment of the electrocautery pen 1800 that relies on the dual suction region mechanism. Electrocautery tip 1804 and suction tip 1818 extend from the distal end 1814 of the housing 1802. Suction connection 1808 and suction tube suction connection 1822, are located at the proximal end 1816 of the electrocautery device 1800.

FIGS. 19A and 19B are a close-up view of the button 1812 and the rotatory diverter 1810. Suction connection 1808 leads to suction channel 1809. Rotary diverter 1810 contains a simple U-shaped passage that connects suction channel 1809 to a proximal suction channel 1860 when spring-loaded button 1812 is in the "retract" state, or distal suction channel 1880 when spring-loaded button 1812 is in the "extend" state. When spring-loaded button 1812 is depressed the rotary diverter swings between the proximal and distal suction channel 1860 and 1880, diverting suction flow between the distal suction region 1852 and the proximal suction region 1856 respectively. The piston 1832, which is mechanically contiguous with the suction tube 1834, slides towards the vacuum, enabling the user to switch the suction tube between retracted and extended positions.

In some embodiments of the electrocautery device, the electrocautery tip can be removed by the user and replaced with tips of different sizes, lengths, and shapes depending on the user's preferences. In some embodiments, the tips are threaded such that they can be screwed and unscrewed into and out of threaded holes in the distal end of the electrocautery device. In other embodiments, the tips snap into corresponding holes in the distal end of the electrocautery device. For the electrocautery tip hole, the requisite electrical connections can be pre-wired around the hole such that an electrical/data connection is formed as soon as the electrocautery tip is in place within the hole.

While the depicted embodiments primarily show the suction tip extending from directly below and extending parallel to the electrocautery tip, embodiments where the suction tip does not extend parallel to the tip and/or from another direction relative to the tip are considered. Embodiments where the suction tube assembly is co-axial with the electrocautery tip are also considered.

In some embodiments of the electrocautery device, the suction tips can be removed by the user and replaced with tips of different sizes, shapes, and lengths depending on the user's preferences and the size, shape, and length of the electrocautery tip attached. For example, the suction tip could have a non-circular, half open, U-shaped tip; one example of these tips can be seem in FIGS. 20D and 20E. The tip could also be angled as seen in the non-limiting example of FIGS. 20A and 20B, rotatable or hinged as seen in the non-limiting example of FIG. 20C, and/or include one or more bends causing the tip to protrude longitudinally from a different position from where the tip initially leaves the housing, as seen in the non-limiting example of FIG. 20E.

Figures 20A, 20B:
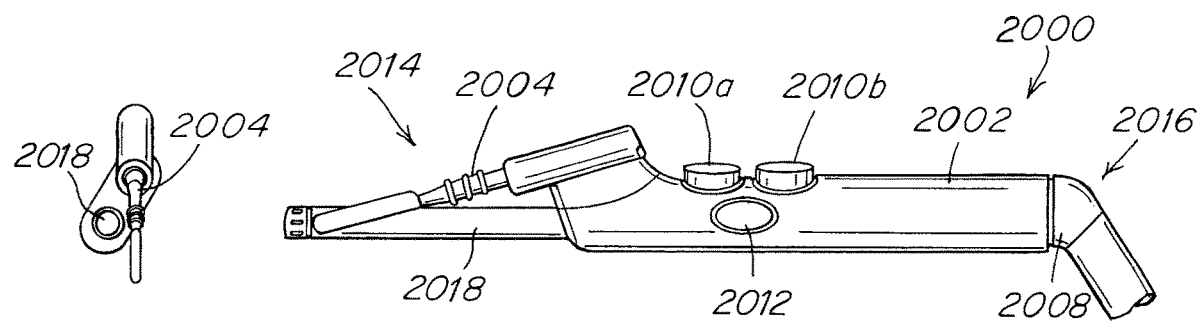
FIG. 20A is a front elevation schematic view according to one embodiment of the electrocautery device.
FIG. 20B is a right side schematic view of the embodiment of FIG. 20A.

FIGS. 20A and 20B show an embodiment of the electrocautery device 2000 with a housing 2002 that curves upwardly at the distal end 2014 such that electrocautery tip 2004 extends at a downward, lateral angle. Also, as best shown in FIG. 20A, the electrocautery tip 2004 and the suction tip 2018 are laterally offset relative to each other such that, when the electrocautery tip is in the extended state, the electrocautery tip does not interfere with suction tip 2018. FIG. 20B shows electrocautery controls 2010a and 2010b, and button 2012 for controlling extension/retraction of the suction tube assembly located just behind the curve of housing 2002, but it should be understood that the buttons could be located anywhere on housing 2002.

Figure 20C:
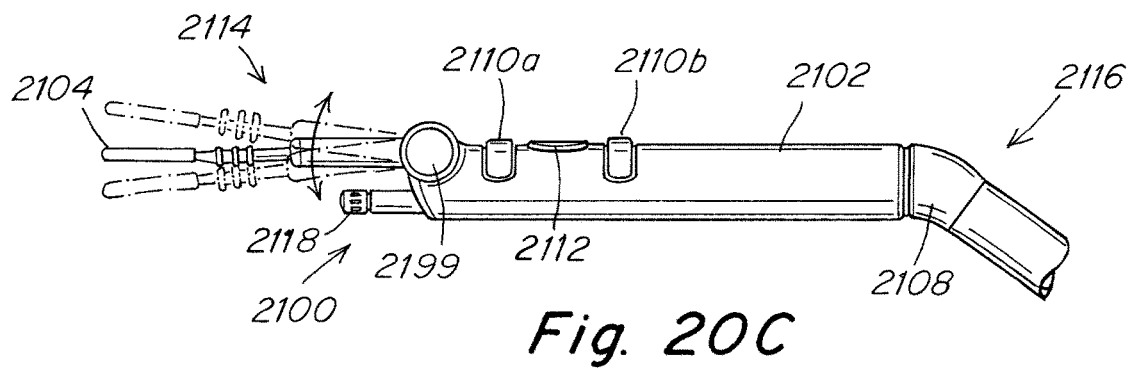
FIG. 20C is a right side schematic view according to one embodiment of the electrocautery device.

FIG. 20C shows an embodiment of the electrocautery device 2100 with a housing 2102 including hinged end 2199 at the distal end 2114 of the device. Electrocautery tip 2104 extends from the hinged end 2199 such that a user can adjust the desired angle for the electrocautery tip. Embodiments including the hinged ends could also have the electrocautery tips laterally offset as in FIG. 20A to avoid interference with suction tip 2118. FIG. 20C shows a different shape for electrocautery controls 2110a and 2110b, but it should be understood that hinged embodiments are not limited to this shape or location of the electrocautery controls or button 2112.

Figures 20D, 20E:
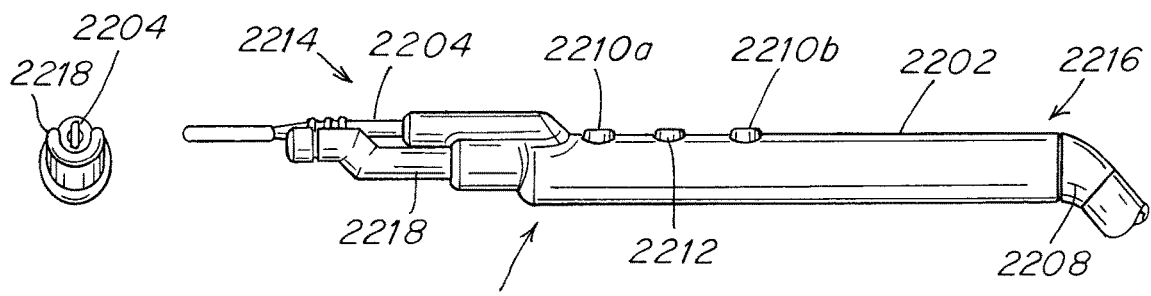
FIG. 20D is a front elevation schematic view according to one embodiment of the electrocautery device.
FIG. 20E is a right side schematic view of the embodiment of FIG. 20D.

FIGS. 20D and 20E show an embodiment of the electrocautery device 2200 with a housing 2202 that includes a partially vertically offset distal end 2214. In these embodiments, electrocautery tip 2204 extends from a position offset from the main portion of the housing 2202. The depicted embodiment also includes a curved, U-shaped, half open suction tip 2218 such that the suction tip originates from a position parallel to the base of the electrocautery tip, but is substantially co-axial to the electrocautery tip 2204 at the distal end of the suction tip, as clearly seen in FIG. 20D. Once again, FIG. 20E shows different possible sizes for electrocautery controls 2210a and 2210b, and button 2212, but it should be understood that the buttons are not limited to any particular shape, size, or arrangement.

Each of FIGS. 20B, 20C, and 20E show embodiments where the distal ends of the electrocautery devices 2000, 2100, and 2200 result in a single suction tube at suction connections 2008, 2108, and 2208. However, as shown in FIGS. 9A and 9B, other embodiments could include multiple suction sources.

In some embodiments, a variety of tips with pre-attached cams can be threaded at the cam end such that they can be screwed into correspondingly threaded piston tubes already set in the electrocautery device. Snap in connections between the suction tip and piston ends are also contemplated. It should be understood that any functional attachment system could be used as long as the user can switch between suction tips.

FIGS. 21A and 21B are perspective views of the electrocautery device according to another embodiment. FIG. 21A shows the electrocautery device with the suction tube in the retracted configuration, while FIG. 21B shows the electrocautery device with the suction tube in the extended configuration. Electrocautery device 2300 includes a housing 2302, an electrocautery tip 2304, and suction tip 2318. The electrocautery tip 2304 and suction tip 2318 extend from the distal end 2314 of the electrocautery device, while a suction connection 2308 extends from the proximal end 2316 of the electrocautery device. Electrocautery controls 2310a and 2310b allow a surgeon or other operator to switch between electrocautery settings. Button 2312 actuates the electrocautery device to cause the suction tip to move between the retracted configuration, wherein the electrocautery tip extends beyond the suction tip, and the extended configuration, wherein the suction tip extends beyond the electrocautery tip.

FIGS. 22A and 22B show cross-sectional views of the electrocautery device of FIGS. 21A and 21B taken along lines 22A and 22B respectively. For ease of reference, the bottom portion of the housing 2302 has been removed from these figures. Electrocautery device 2300 includes suction tube assembly 2390, having a proximal section 2334 disposed generally within suction cavity 2320 (which is defined at least partially by the removed bottom portion of the housing 2302), and a distal section 2330 disposed generally within suction tip cavity 2338. An enlarged rear cavity 2350 is in fluid communication with suction connection 2308. In this embodiment, the rear cavity 2350 is sized to be larger in diameter than the diameter of the suction tube and is longer in length than the longitudinal extent of movement of the suction tip. A bottleneck portion 2352 is disposed about the suction tube in order to suitably fluidly seal off rear cavity 2350 from suction cavity 2320 while allowing the suction tube to translate through the bottleneck, back and forth along its longitudinal axis. As the suction tube assembly 2390 slides back and forth, the proximal end 2348 always stays within rear cavity 2350, meaning that the proximal end of the suction tube never slides distally beyond the bottleneck 2352. Gas or fluid that is drawn into suction tip 2318 drains out the proximal end 2348 of the suction tube assembly, possibly resting temporarily in the rear cavity 2350 before being sucked from the electrocautery device entirely by the suction source. In the retracted configuration, the proximal end of the suction tube is located near the proximal end of rear cavity 2350, and could even extend partially into suction connection 2308 as seen in 22A. In this retracted configuration, vacuumed fluid and gas entering the suction tip 2318 is expelled from the suction tube mostly directly into suction connection 2308, but some fluid or gas could temporarily remain in rear cavity 2350 depending on the strength of the suction force, before being further vacuumed to the suction source entirely. When the suction tube is in the extended configuration as seen in FIG. 22B, the proximal end of the suction tube is located towards the distal end of rear cavity 2350, proximal to bottleneck 2352. In this configuration, fluid and gas that is vacuumed through suction tip 2318 is expelled into rear cavity 2350 before being removed from the rear cavity by suction force drawing the fluid and gas towards the suction connection 2308 and to the suction source. In this way, the suction tube telescopes within the suction cavity, thereby effectively allowing the suction tip to move to the extended position while still allowing vacuum communication to allow evacuation of fluids and gases from the surgical site. Thus, in this embodiment, the telescoping feature of the suction tube within the rear cavity replaces the bellows described above.

Figure 23A:
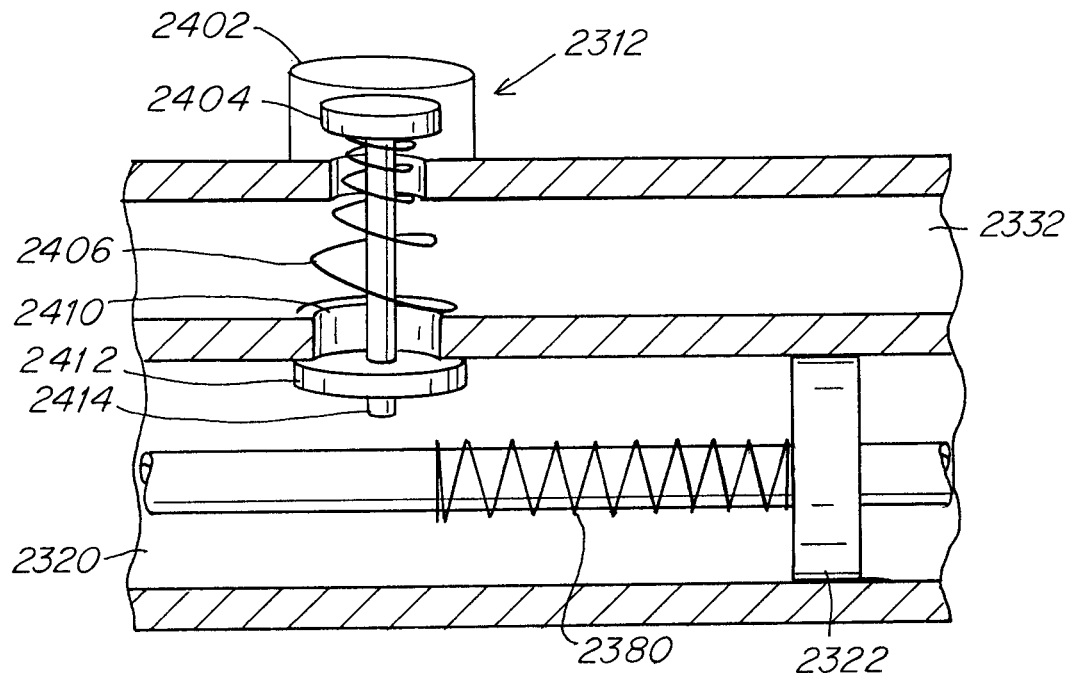
FIG. 23A is an enlarged schematic view of the area encircled by line 23A of FIG. 22A.
Figure 23B:
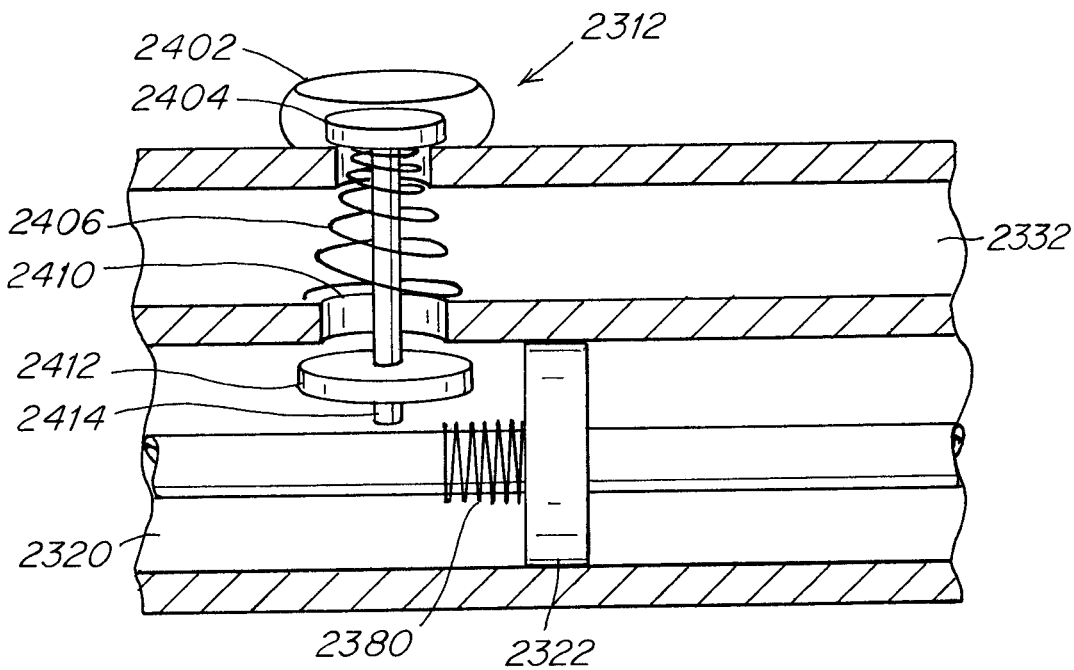
FIG. 23B is an enlarged schematic view of the area encircled by line 23B of FIG. 22B.

FIG. 23A is an enlarged view of a portion of the device 2300 showing the button 2312 of FIG. 22A used to actuate the suction tube. In this embodiment, the button includes a button head 2404 which is covered by button cover 2402. The button cover is flexible to allow a user to depress button head 2404 by reversibly deforming the button cover. Depressing the button causes button head 2404 and button pin 2414 to translate in the direction of depression, depressing button spring 2406 such that when the button is released, the button head 2404 returns to its undepressed position. In the undepressed position shown in FIG. 23A, gasket 2412 blocks port 2410. When the button pin 2414 translates in the direction of depression, gasket 2412 translates with the button pin, unblocking port 2410 and allowing the suction source to create a vacuum in suction cavity 2320, distal to the piston 2322, via suction channel 2332. With the presence of the vacuum now in suction cavity 2320, piston 2322 slides distally, compressing spring 2380. Releasing button head 2404 causes button pin 2414 to return to its original position, causing gasket 2412 to once again seal off suction cavity 2320 from suction channel 2332. Without the active vacuum, no more suction force acts on the piston, allowing the force from spring 2380 to push the piston in the proximal direction, as described below.

In this embodiment, suction tube assembly 2390 is configured to utilize the aforementioned click-lock system shown in depth in FIGS. 6A to 6C and 7A to 7C. As in prior embodiments, and referring again to FIGS. 22A and 22B, distal section 2330 includes cam 2356 at its proximal end, and suction tip 2318 at its distal end. The proximal section 2334 has cam teeth 2340 at its distal end and extends into rear cavity 2350 at its proximal end 2348.

Thus, when a user triggers button 2312, suction channel 2332 connects the suction source to the front of suction cavity 2320, causing a vacuum force to cause piston 2322 and suction tube assembly 2390 to slide distally. When the suction tube assembly slides distally, the sloped edges of cam teeth 2340 push against cam 2356, causing the cam to slide distally and to rotate about the longitudinal axis of the suction tube assembly. As previously described, the cam could rotate into alignment with locking grooves in the housing, or rotate out of alignment with the locking grooves depending on whether the device was in the retracted configuration or the extended configuration. When the user releases button 2312, the suction cavity 2320 is allowed to equilibrate with the environment as described below, allowing the spring 2380 to act on the piston 2322 and cause the suction tube assembly 2390 to slide proximally. As previously described, as the tube moves to the extended configuration, the cam slides proximally into the locking grooves, locking the tube in the extended configuration. To retract the tube, the button is again triggered, causing a vacuum force to cause piston 2322 and suction tube assembly 2390 to slide distally. When the suction tube assembly slides distally, the cam and cam teeth cooperate in a manner to essentially unlock the suction tube (as described in the above embodiments). Once the button is released, the piston slides fully proximally to retract the tube.

Figure 24:
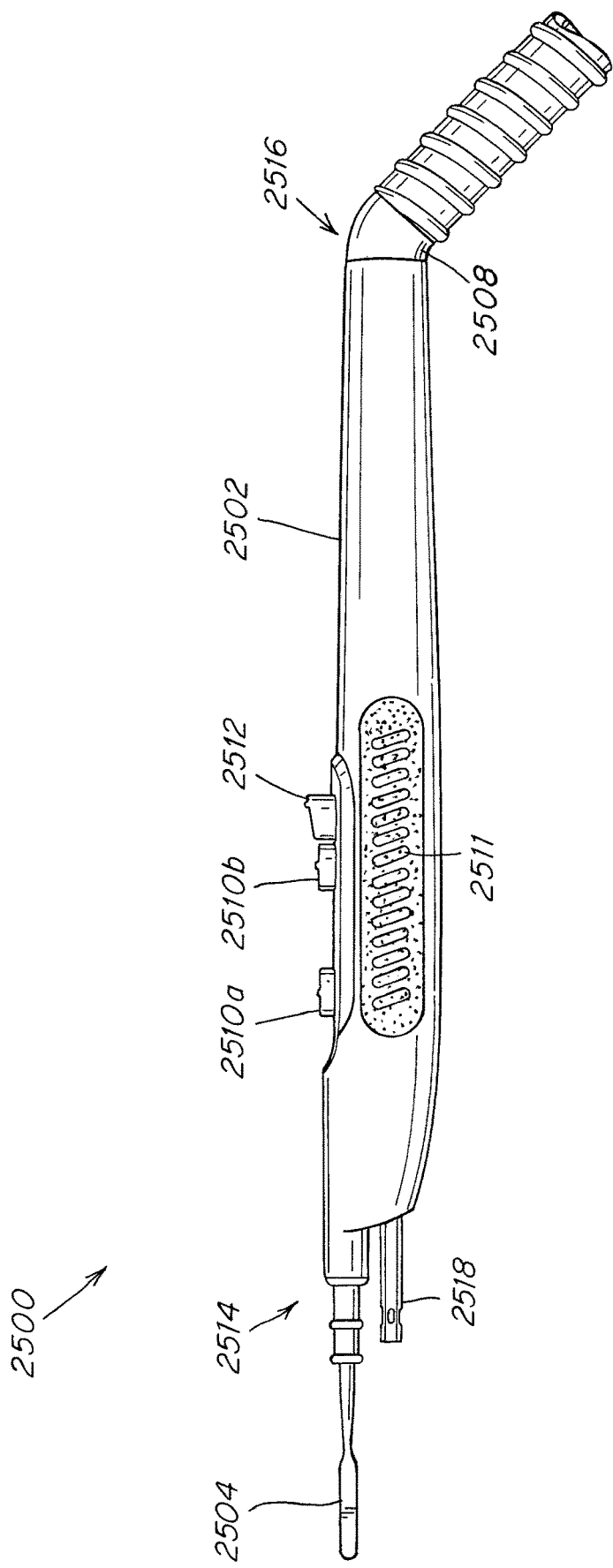
FIG. 24 is a side elevation view of the electrocautery device according to one embodiment.

FIG. 24 is a side elevation view of the electrocautery device 2500 according to one embodiment. The electrocautery device 2500 includes housing 2502, electrocautery tip 2504 and suction tip 2518, which extends from the distal end 2514 of the device, and suction connection 2508 at the proximal end 2516 of the device. Electrocautery controls 2510a, 2510b and button 2512, which toggles the suction tube 2518 between the retracted configuration and the extended configuration, are located on housing 2052. Grip pad 2511, which in one embodiment has a series of raised ribs, is disposed on the side of housing 2502. The grip pad may be made of a softer material than the housing and in one embodiment may be made of silicone rubber. The grip pad may allow a user to maintain a more secure grip of the electrocautery device 2500 during use and/or provide comfort for a user as the user grasps and holds the device.

In one embodiment shown in FIG. 24, button 2512 is sloped upwards from distal to proximal and located directly proximal to electrocautery control 2510b. The inventors have contemplated that this arrangement of button 2512 could facilitate allowing a user to easily trigger button 2512 by simply rocking their finger when the finger is in place over electrocautery control 2510b. In this way, the surgeon's finger need not be displaced significantly, thereby having the potential to reduce joint stress and fatigue throughout the surgery, given that toggling between actuating the suction tip and actuating the electrocautery tip can occur hundreds of times during surgery. In one embodiment, the electrocautery controls and the button are located along the midline of the device. It is contemplated that placing the buttons at the midline of the device allows the buttons to be easily located by both left-handed and right-handed users. However, other embodiments with the electrocautery controls and the buttons located on the sides of the device, to favor either left or right handed users, are also contemplated. Other non-traditional button arrangements are contemplated as well. For instance, instead of a button, toggling can be triggered by squeezing depressible triggers along the sides of the housing, or by rolling a dial along the side of the device. Other controls for triggering configuration toggling are contemplated as well. Similarly, other embodiments with other shapes and locations for the toggling button and electrocautery controls are contemplated with some examples described and shown above in regards to previous embodiments.

While the previous mechanisms were described as relating to non-laparoscopic electrocautery devices with suction capability, it should be understood that the teachings of the current disclosure can be applied to laparoscopic electrocautery devices with suction applications as well. For example, such laparoscopic embodiments may include a suction tube assembly that is actuated between extended and retracted configurations using the above-described vacuum suction as the motive force to move the suction tube between positions. The device can be connected to a suction source in a manner consistent with existing laparoscopic devices, and the suction source would be used to actuate the suction tube assembly using the above described mechanisms. In some embodiments, such a laparoscopically enabled device may be similar in construction to the previously described embodiments, but the suction tube may be coaxial with the electrocautery tip, which in turn may be sized and shaped to be extendible into working sites through surgical incisions while a surgeon operates electrocautery controls, suction controls, and retraction or extension of the suction tube from outside of the working site.

FIGS. 25A-25B, 26A-26B, and 27A-27B show one embodiment of the electrocautery device 2700 that may be configured for laparoscopic applications. Electrocautery device 2700 includes a housing 2702, an elongate outer tube 2780 extending from the housing, and an electrocautery tip 2704 extending from the elongate outer tube 2780. A suction tip 2718 is disposed at the distal end of the inner tube 2781. The device 2700 also includes an elongate inner tube 2781 that is coaxial with outer tube 2780. The outer tube 2780 may have sufficient length such that the distal end of the outer tube may extend into a body cavity through a surgical incision, while the housing of the electrocautery device 2700 remains outside of the body cavity and at a suitable distance from the body cavity to allow a surgeon to operate. In some embodiments, the outer tube may be approximately 8-12 inches long, but other lengths are also contemplated. The outer tube may have a diameter of approximately 5-10 mm and capable of being fit within a trocar, but other diameters are contemplated. The inner tube 2781 may extend coaxially with the outer tube 2780, and/or the electrocautery tip 2704, and further may be continuous with a suction tube assembly within the housing as will be described below. The housing 2702 includes a suction connection 2708 extending from the proximal end 2716 of the electrocautery device. Electrocautery controls 2710a and 2710b are disposed on the housing and allow a surgeon or other operator to switch between electrocautery settings. Suction toggle 2712 actuates the electrocautery device to cause the inner tube 2781 to move between the retracted position within outer tube 2780 and the extended position protruding from outer tube 2780. When the inner tube is in the retracted position, the electrocautery tip 2704 becomes exposed distally beyond the suction tip 2718. When the inner tube is in the extended position, the suction tip 2718 extends distally beyond the electrocautery tip 2704, thereby concealing the electrocautery tip. Although the suction tube is configured to extend and retreat thereby shrouding or exposing the electrocautery tip 2704, the present disclosure is not so limited and the device may be configured such that the electrocautery tip is moveable between retreated and extended position relative to the distal end of the suction tip.

FIGS. 26A and 26B show cross-sectional views of the electrocautery device of FIGS. 25A and 25B taken along lines 26A and 26B respectively. Electrocautery device 2700 includes suction tube assembly 2790, having a proximal section 2734 disposed generally within a suction cavity 2720, and a distal section 2730 disposed generally within suction tip cavity 2738. The distal section 2730 includes inner tube 2781, extending from the distal end of the housing 2702. Rear cavity 2750 may be fluidly continuous with suction connection 2708 and also fluidly continuous with the proximal end 2748 of the suction tube assembly 2790, thus conducting suction force from the suction source to the suction tip 2718. Gas or fluid that is drawn into suction tip 2718 may drain out of the proximal end 2748 of the suction tube assembly before being sucked from the electrocautery device entirely by the suction source.

As previously described, when the inner tube is in the retracted position, as shown in FIG. 26A, if the user triggers suction toggle 2712, the suction source may be allowed to create a vacuum in the suction cavity 2720, distal to the piston 2722, via suction channel 2732. With the presence of the vacuum in suction cavity 2720, piston 2722 slides distally and may bring suction tip 2718 to the extended position extending beyond electrocautery tip 2704. Releasing suction toggle 2704 may fluidly disconnect suction cavity 2720 from suction channel 2732, allowing air to fill the vacuum in the suction cavity. Without the active vacuum, no more suction force acts on the piston, allowing a spring (not shown in FIGS. 26A and 26B) distal to the piston to return the piston to the piston's original position. As such, the suction tube assembly is slid proximally, retracting the inner tube and bringing the suction tip 2718 to the retracted position retracted within outer tube 2780.

In this embodiment, suction tube assembly 2790 may be configured to utilize the aforementioned click-lock system shown in depth in FIGS. 6A to 6C and 7A to 7C for laparoscopic applications. As in prior embodiments, and referring again to FIGS. 26A and 26B, distal section 2730 includes cam 2756 at its proximal end, and suction tip 2718 at its distal end. The proximal section 2734 may have cam teeth 2740 at its distal end and extends into rear cavity 2750 at its proximal end 2748.

Thus, when a user triggers suction toggle 2712, suction channel 2732 connects the suction source to the front of suction cavity 2720, causing a vacuum force to cause piston 2722 and suction tube assembly 2790 to slide distally. When the suction tube assembly slides distally, the sloped edges of cam teeth 2740 may push against cam 2756, causing the cam to slide distally and to rotate about the longitudinal axis of the suction tube assembly. As previously described, the cam could rotate into alignment with locking grooves in the housing, or rotate out of alignment with the locking grooves depending on whether the device was in the retracted configuration or the extended configuration. When the user releases suction toggle 2712, the suction cavity 2720 is allowed to equilibrate with the environment as described above, allowing the spring (not shown) to act on the piston 2722 and cause the suction tube assembly 2790 to slide proximally. As previously described, as the suction tube assembly moves to the extended configuration, the cam slides proximally into the locking grooves, locking the tube in the extended configuration. To retract the tube, the suction toggle is again triggered, causing a vacuum force to cause piston 2722 and suction tube assembly 2790 to slide distally. When the suction tube assembly slides distally, the cam and cam teeth cooperate in a manner to essentially unlock the suction tube (as described in the above embodiments). Once the suction toggle is released, the piston slides fully proximally to retract the tube.

Laparoscopic surgeries often require the body cavity to be maintained at a relatively constant state of inflation. Accordingly, the inventors have contemplated that it may be advantageous to include a mechanism for shutting off suction for the electrocautery device for use of the electrocautery device in laparoscopic applications. As best seen in FIGS. 27A and 27B, some embodiments of the electrocautery device may include suction button 2713. In these embodiments, suction connection 2708 may be fluidly connected to rear cavity 2750 and to the proximal end of the suction tube assembly 2748 by compressible section 2791. When compressible section 2791 is uncompressed, suction may continue uninterrupted from the suction source to the rear cavity 2750 and suction tube assembly 2790. When the compressible section 2791 is compressed, fluid flow becomes obstructed, cutting off suction from rear cavity 2750 and suction assembly 2790. As such, when the compressible section is compressed, the suction tip 2718 no longer draws in fluid or gas.

To accomplish pinching of the compressible section 2791, suction button 2713 may be operatively connected to a hammer 2792 such that pressing suction button 2713 moves hammer 2792 between a depressed position where hammer 2792 compresses compressible section 2791, and a raised position where hammer 2792 releases compressible section 2791. As such, the user may press suction button 2713 to activate suction from suction tip 2718 when desired, and may release suction button 2713 again to cease suction when no longer needed.

In some embodiments, suction button 2713 may be connected to hammer 2792 by a lever 2793 such that depressing the suction button 2713 mechanically lifts hammer 2792. Suction button 2713 may be spring loaded in some embodiments such that depressing the suction button 2713 locks the button in place, but depressing the suction button a second time unlocks the button and causes the button to spring back to the original undepressed position. Alternatively, suction button 2713 may be configured such that it must be held down to allow vacuum flow in compressible section 2791. When released, a spring (not shown) returns suction button 2713 to its released position which causes lever 2793 to actuate hammer 2792 to pinch the compressible section 2791. The spring (not shown) may be operatively coupled to the suction button 2713 and may be of suitable spring force to cause the hammer 2792 to compress the compressible section. It should be appreciated that in one embodiment, the compressible section 2791 may be a tube, whereby pinching the tube seals off flow of fluid arising from at least suction from the suction source.

It should be understood however that other methods of triggering movement of the hammer are contemplated. For example, pressing suction button 2713 could trigger a signal to lift or otherwise move hammer 2792 via an actuator. Other methods are contemplated and the current application is not so limited. Actuation mechanisms described in relation to other embodiments above may also be applied to actuation of the hammer.

Although the above embodiments are described to focus on actuating a suction tube assembly using suction, it should be appreciated that the teachings could be applied to actuating any portion of an electrocautery device, or more broadly to actuate components of any medical device or other device. For example, in an electrocautery wand, the device may be configured such that the electrocautery tip could be extended beyond a suction tip or retracted behind a suction tip by actuating the electrocautery tip using suction in a manner consistent with the above described mechanisms. Similarly, for other surgical devices, the suction actuation teachings of the current disclosure can be applied to actuate forceps, scissors, cameras, or other appropriate components of a suction enabled device.

Figure 28A:
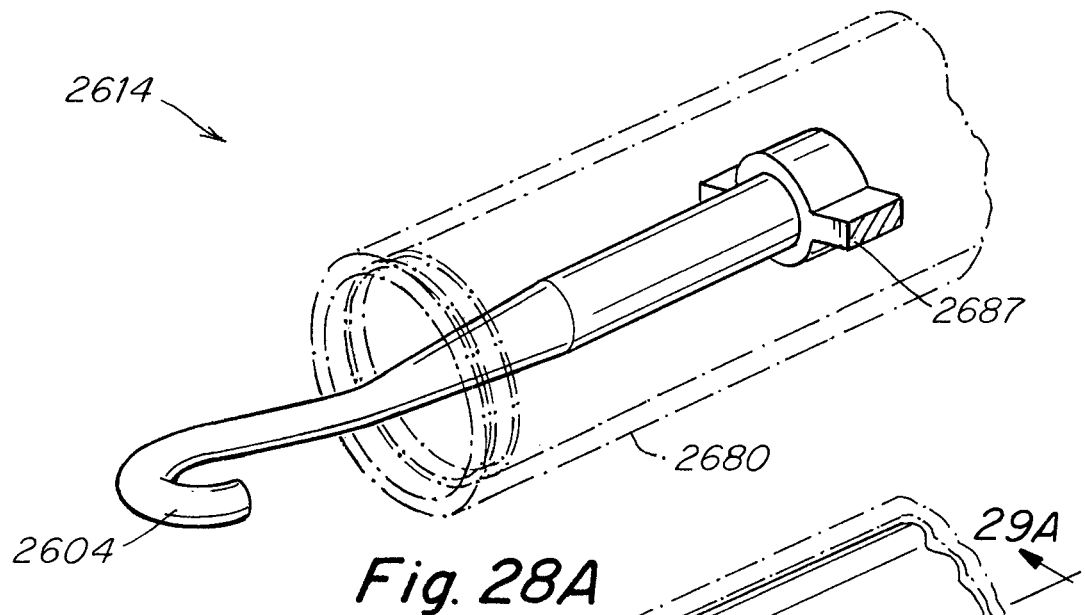
FIG. 28A is an enlarged view of a distal tip of the electrocautery device of FIG. 25A with the outer tube shown in transparent.
Figure 28B:
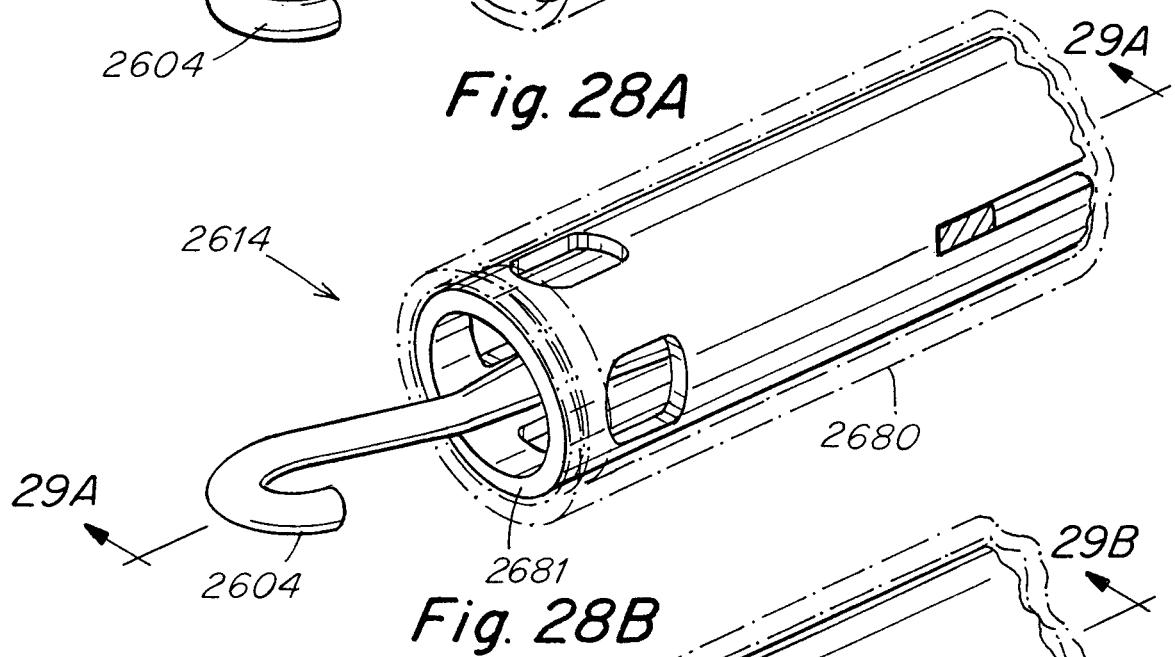
FIG. 28B is an enlarged view of the distal tip of the electrocautery device of FIG. 25A with the inner tube in the retracted position and the outer tube shown in transparent.
Figure 28C:
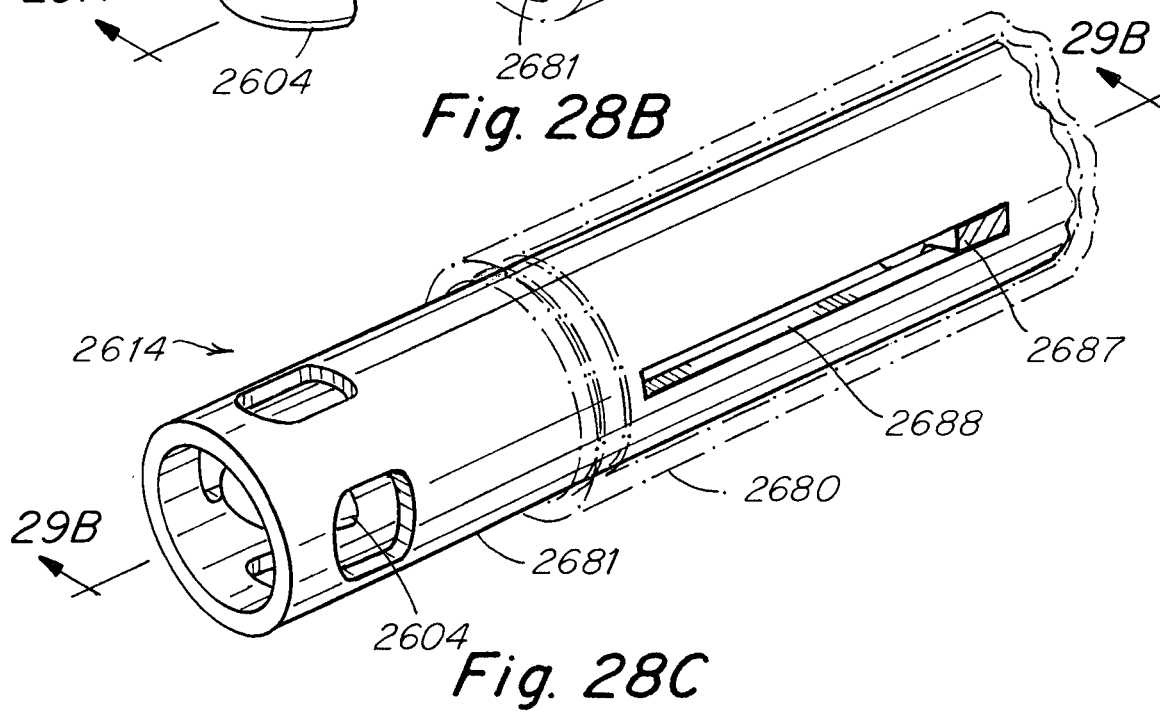
FIG. 28C is an enlarged view of the distal tip of the electrocautery device of FIG. 25A with the inner tube in the extended position and the outer tube shown in transparent.
Figure 29A:
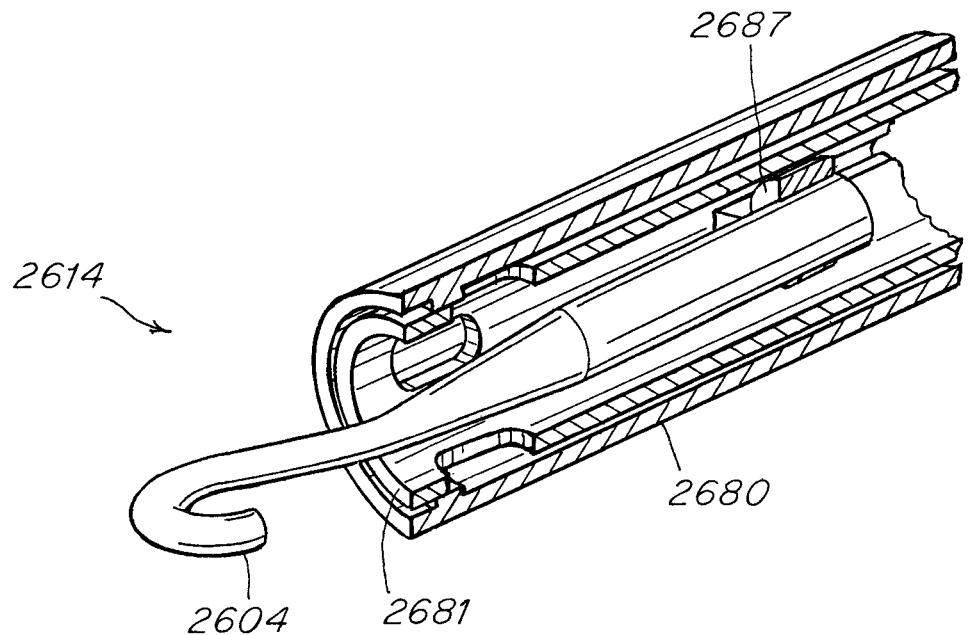
FIG. 29A is an enlarged cross-sectional view of the distal tip of the electrocautery device of FIG. 28A taken along line 29A.
Figure 29B:
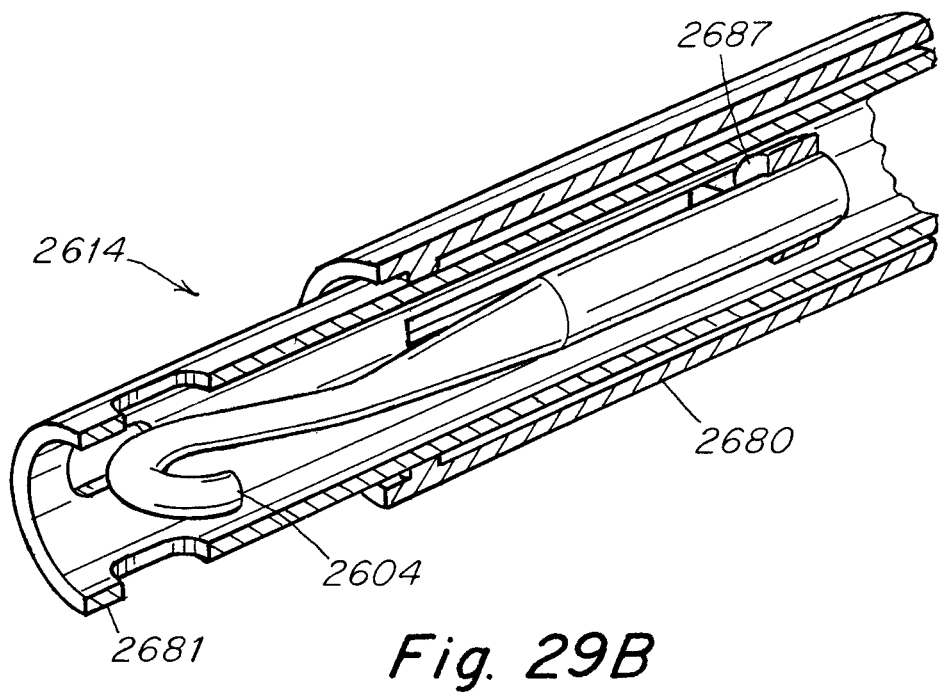
FIG. 29B is an enlarged cross-sectional view of the distal tip of the electrocautery device of FIG. 28B taken along line 29B.

FIGS. 28A-28C and 29A-29B show the distal tip 2614 of the electrocautery device 2700. In FIG. 28A, the inner tube is not shown and the outer tube is shown in phantom. In FIGS. 28B, 28C, 29A and 29B, the inner tube 2681 in one of the extended or retracted positions. Electrocautery tip 2604 may extend from the distal end of the outer tube 2680. When the suction tip 2618 is in the retracted position, the inner tube 2681 is retracted within outer tube 2680. When the inner tube is retracted, electrocautery tip 2804 may be the distal most feature, allowing a user to work with the electrocautery tip unhindered by the inner tube. When the suction tip 2618 is in the extended position, the inner tube 2681 extends from outer tube 2680 over electrocautery tip 2814. When the inner tube extends, the distal end of the inner tube 2681 becomes the distal most feature, allowing the user to suction without interference from the electrocautery tip.

In some embodiments, electrocautery tip 2604 may be secured to the outer tube 2680 by anchor 2687. Anchor 2687 of the depicted embodiment may be a cuff extending from the inner surface of the outer tube 2680. The inner tube 2681 may include elongate slots 2688 that may accommodate the anchor 2687 such that anchor 2687 may be attached to the outer tube while the inner tube may be free to translate between the extended and retracted positions without anchor 2687 obstructing movement of the inner tube. As such, the inner tube is free to translate relative to the outer tube while the electrocautery tip remains stationary relative to the outer tube. It should be understood that the electrocautery tip may be attached to the adaptor in any way that does not hinder movement of the inner tube.

In some embodiments, the inner surface of outer tube 2680 and anchor 2687 may be conductive. In these embodiments, electrical power may be transmitted from the electrocautery device to the electrocautery tip 2604 via the inner conductive surface of the outer tube 2680 and anchor 2687. The outer surface of the outer tube 2680 and inner tube 2681 may be insulated.

Other methods for transmitting power to the electrocautery tip are contemplated. For example, a wire may be disposed along the inner surface of the outer tube, between the inner tube and the outer tube, from the electrocautery device to the electrocautery tip to deliver electrical power to the electrocautery tip.

The inner and outer tubes of the adaptor may be formed of any material suitable for surgical applications and allow the device to have sufficient rigidity to structurally withstand the forces expected during surgical use.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Also, while embodiments herein are described with respect to controlling flow of air in the device to move the suction tip, it should be appreciated that the other gases in the surgical field may flow in the device to cause the desired movement of the suction tip. In other words, the use of the terms "air" and "airflow" should not be considered as being limited to air, as other gases in the environment/surgical site may be present.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An electrocautery and suction device comprising:
a housing connectable to a vacuum source, the housing including a suction cavity;
an electrocautery tip connected to the housing;
a suction tube assembly movable from a retracted position to an extended position relative to the housing, the suction tube assembly including a suction tip;
an actuator constructed and arranged to selectively form a vacuum in the suction cavity in cooperation with the vacuum source to exert a suction force on the suction tube assembly to cause the suction tip to move from the retracted position to the extended position; and
a click-lock mechanism constructed and arranged to mechanically lock the suction tip in the extended position upon triggering of the actuator, wherein the suction tip remains in the extended position upon release of the actuator and is constructed and arranged to mechanically unlock the suction tip upon triggering the actuator, wherein the suction tip moves into the retracted position.

2. The electrocautery and suction device of claim 1, wherein the suction cavity communicates with a vent, and wherein the actuator is constructed and arranged to block communication of the suction cavity and the vent causing the vacuum in the suction cavity.

3. The electrocautery and suction device of claim 2, further comprising a channel disposed in the housing adapted to communicate with the vent and the suction cavity.

4. The electrocautery and suction device of claim 1, wherein the suction tube assembly includes a piston, moveable by the vacuum, the piston being constructed and arranged to move the suction tip between the extended and retracted positions.

5. The electrocautery and suction device of claim 4, wherein the suction tube assembly includes a cam operatively connected to the suction tip.

6. The electrocautery and suction device of claim 5, wherein the piston is constructed and arranged to push the cam in a longitudinal direction.

7. The electrocautery and suction device of claim 6, wherein the cam is constructed and arranged to rotate between a lockable and an non-lockable state when the piston pushes on the cam.

8. The electrocautery and suction device of claim 1, wherein the suction tube assembly includes a piston, moveable by the vacuum, the piston being constructed and arranged to move the suction tip between the extended and retracted positions, wherein the piston is spring biased against the suction force.

9. The electrocautery and suction device of claim 1, wherein the suction tube assembly further includes an elongate tube, and the suction tip is constructed and arranged to be removable from the elongate tube.

10. The electrocautery and suction device of claim 9, further comprising a plurality of suction tips, each having an alternate shape, wherein a suction tip of one shape is replaceable with a suction tip of an alternate shape.

11. The electrocautery and suction device of claim 1, wherein, in the extended position, the suction tip extends longitudinally beyond the electrocautery tip.

12. The electrocautery and suction device of claim 1, wherein a proximal end of the suction tube assembly connects to the vacuum source via a bellows, and the bellows expands or contracts as the suction tip moves between the retracted position and the extended position.

13. The electrocautery and suction device of claim 1, wherein a proximal end of the suction tube assembly extends into a rear cavity of the housing that fluidly connects with the vacuum source, and the proximal end of the suction tube assembly remains in the rear cavity when the suction tip is in the retracted position or in the extended position.

14. The electrocautery and suction device of claim 13, wherein the electrocautery and suction device is configured to vacuum fluid into the suction tip, wherein the fluid enters the rear cavity before being vacuumed from the electrocautery and suction device by the vacuum source.

15. The electrocautery and suction device of claim 1, further comprising an elongate outer tube connected to the housing, wherein the electrocautery tip extends from the elongate outer tube.

16. The electrocautery and suction device of claim 15, further comprising an elongate inner tube, wherein the suction tip is fluidly connected to the suction tube assembly by the elongate inner tube.

17. The electrocautery and suction device of claim 16, wherein the elongate inner tube is coaxial with the elongate outer tube.

18. The electrocautery and suction device of claim 1, further comprising a compressible tube fluidly connected between a proximal end of the suction tube assembly and the vacuum source, wherein the compressible tube is constructed and arranged to be compressed to selectively block fluid communication between the suction tube assembly and the vacuum source.

19. The electrocautery and suction device of claim 18, further comprising a hammer constructed and arranged to selectively compress the compressible tube.

20. The electrocautery and suction device of claim 19, further comprising an actuator and a lever, wherein the hammer is operatively coupled to the lever whereby selectively actuating the actuator causes the lever to move the hammer.

21. An electrocautery and suction device comprising:
a housing connectable to a vacuum source, the housing including a suction cavity;
an electrocautery tip connected to the housing;
a suction tube assembly movable from a retracted position to an extended position relative to the housing, the suction tube assembly including a suction tip and a piston; and
an actuator constructed and arranged to selectively form a vacuum in the suction cavity in cooperation with the vacuum source to exert a suction force on the suction tube assembly to cause the suction tip to move from the retracted position to the extended position, wherein the suction tip is constructed and arranged to be mechanically locked in the extended position, wherein the piston is moveable by the vacuum, the piston being constructed and arranged to move the suction tip between the extended and retracted positions, wherein the suction tube assembly includes a cam operatively connected to the suction tip, wherein the piston is constructed and arranged to push the cam in a longitudinal direction, and wherein the cam is constructed and arranged to rotate between a lockable and an non-lockable state when the piston pushes on the cam.

* * * * *